(12) United States Patent
Walters et al.

(10) Patent No.: US 8,877,156 B2
(45) Date of Patent: Nov. 4, 2014

(54) CONTRAST AGENTS ANCHORED BY THIOLS ON NANOPARTICLES

(75) Inventors: Marc A. Walters, New Rochelle, NY (US); Youssef Zaim Wadghiri, New York, NY (US)

(73) Assignee: New York University, New York, NY (US)

(*) Notice: Subject to any disclaimer, the term of this patent is extended or adjusted under 35 U.S.C. 154(b) by 1173 days.

(21) Appl. No.: 12/146,879

(22) Filed: Jun. 26, 2008

(65) Prior Publication Data

US 2009/0162275 A1 Jun. 25, 2009

Related U.S. Application Data

(60) Provisional application No. 60/946,288, filed on Jun. 26, 2007.

(51) Int. Cl.
*A61K 51/12* (2006.01)
*A61K 49/00* (2006.01)
*A61K 49/18* (2006.01)

(52) U.S. Cl.
CPC ......... *A61K 49/1878* (2013.01); *A61K 51/1255* (2013.01)
USPC .......................................... 424/1.29; 424/9.1

(58) Field of Classification Search
None
See application file for complete search history.

(56) References Cited

U.S. PATENT DOCUMENTS

| 5,985,271 A | 11/1999 | Fischetti et al. |
| 6,274,552 B1 | 8/2001 | Tamarkin et al. |
| 6,366,033 B1 * | 4/2002 | Greci et al. .................. 315/363 |
| 6,805,865 B1 | 10/2004 | Holaday et al. |
| 2002/0187172 A1 | 12/2002 | Reb et al. |

FOREIGN PATENT DOCUMENTS

| WO | 93/24141 A1 | 12/1993 |
| WO | 98/05672 A1 | 2/1998 |
| WO | 99/24066 A2 | 5/1999 |
| WO | 99/24077 A2 | 5/1999 |
| WO | 02/087509 A2 | 11/2002 |
| WO | 2005/065121 A2 | 7/2005 |
| WO | 2005/072893 A1 | 8/2005 |

OTHER PUBLICATIONS

Ipe BI, Yoosaf K, Thomas KG. Functionalized gold nanoparticles as phosphorescent nanomaterials and sensors. 2006 J. Am. Chem. Soc. 128: 1907-1913.*
Mandal S, Gole A, Lala N, Gonnade R, Ganvir V, Sastry M. Studies on the reversible aggregation of cysteine-capped colloidal silver particles interconnected via hydrogen bonds. 2001 Langmuir 17: 6262-6268.*
Lu ZR, Wang X, Parker DL, Goodrich KC, Buswell HR. Poly(l-glutamic acid) Gd(III)-DOTA conjugate with a degradable spacer for magnetic resonance imaging. 2003 Bioconjug. Chem. 14: 715-719.*
Entry for "polymer". Hawley's Condensed Chemical Dictionary. 2002 John Wiley & Sons, Inc. 14th edition. Accessed May 17, 2012.*
Paciottoti et al., "Colloidal Gold: A Novel Nanoparticle Vector for Tumor Directed Drug Delivery," Drug Delivery 11:169-183 (2004).

* cited by examiner

*Primary Examiner* — Michael G Hartley
*Assistant Examiner* — Jennifer Lamberski
(74) *Attorney, Agent, or Firm* — LeClairRyan, a Professional Corporation

(57) ABSTRACT

The present invention is directed toward a multivalent product including a nanoparticle with a metal, metal alloy, or metal oxide core, a plurality of non-polymerizing ligands bound to the nanoparticle, and a plurality of paramagnetic ions coupled to the nanoparticle by the ligands. Methods of making and using the multivalent product are also disclosed.

26 Claims, 45 Drawing Sheets

CONTRAST AGENTS ANCHORED BY THIOLS ON NANOPARTICLES

The present application claims benefit of U.S. Provisional Application Ser. No. 60/946,288, filed Jun. 26, 2007, which is hereby incorporated by reference in its entirety.

FIELD OF THE INVENTION

The present invention relates to contrast agents anchored by thiols on nanoparticles.

BACKGROUND OF THE INVENTION

Gadolinium containing complexes formed with the ligands diethylenetriaminepentaacetic acid (DTPA) or 1,4,7,10-tetracarboxymethyl-1,4,7,10-tetraazacyclododecane (DOTA) provide complexes known as Magnevist™ and Dotarem™, respectively, which are approved for clinical applications. In their unmodified form, they are radiologically efficacious but non-specific agents suitable for the acquisition of MRI images of the circulatory system (the "blood pool") and abnormalities therein. See Jacques, V., et al., *Contrast Agents I,* 221: 123-164 (2002) and Clarkson, R. B., *Contrast Agents I,* 221: 201-235 (2002). Most common contrast agents (CA) derive from modifications of DTPA and DOTA to endow them with specificity towards certain tissues and cells. See Jacques, V., et al., *Contrast Agents I,* 221: 123-164 (2002). In principle, high contrast and specificity is accessible with multivalent particles that contain multiple surface lanthanide complexes and multiple targeting groups to augment contrast and tissue specificity, respectively. See Woods, M., et al., *Chem. Soc. Rev.,* 35(6): 500-511 (2006); Weissleder, R., et al., *Nat. Biotechnol.,* 23(11): 1418-1423 (2005); and Caplan, M. R., et al., *Ann. Biomed. Eng.,* 33(8): 1113-1124 (2005).

Silver or gold nanoparticles, are ideal for the preparation of multivalent constructs. Robust attachment on the surface of these metal particles is achieved through phosphine, amine, carboxylate, thiol, or thioether linkages. See Glomm, W. R., *Journal of Dispersion Science and Technology,* 26(3): 389-414 (2005) and Hostetler, M. J., et al., *Current Opinion in Colloid & Interface Science,* 2(1): 42-50 (1997).

Molecules, and chelating moieties in particular, can attach to the surface of Ag or Au nanoparticles through sulfur linkages via physi- and chemisorption. See Lavrich, D. J. et al., *J. Phys. Chem. B,* 102(18): 3456-3465 (1998) and Pederson, D. B., et al., *J. Phys. Chem. A,* 109(49): 11172-11179 (2005). The practice of binding thiols to these particular metals either in their bulk phases or as nanoparticles is very well developed. See Ulman, A., *Chemical Reviews (Washington D.C.),* 96(4): 1533-1554 (1996). Similarly extensive are the methods for producing nanoparticles that are highly monodisperse, which is important to ensure a uniform response when the agent is administered to an organism. See Brust, M., et al., *Colloids and Surfaces, A: Physicochemical and Engineering Aspects,* 202(2-3): 175-186 (2002) and Daniel, M.-C., et al., *Chemical Reviews (Washington D.C.),* 104(1): 293-346 (2004). The ultimate constructs consisting of surface derivatized metal particles are known as core-shell assemblies which are similarly monodisperse when the surface is of uniform thickness. Certain core-shell assemblies to be discussed are of potential importance as imaging agents for MRI. The colloidal assemblies discussed below are constructed of nanoparticulate and molecular components that are clinically approved, which may expedite the eventual approval of efficacious imaging agents that result from the proposed research.

In the early decades of the 20th century, colloidal gold was used to treat rheumatoid arthritis. See Salter, R. B., et al., *Immune React. Exp. Models Rheum. Dis., Proc. Can. Conf. Res. Rheum. Dis.,* $4^{th}$, 165-173 (1972) and Tarsy, J. M., *J. Lab. Clin. Med.,* 26: 1918-1924 (1941). In recent years, gold colloids have been used for immunodiagnostics and histology. See Daniel, M.-C., et al., *Chemical Reviews (Washington D.C.),* 104(1): 293-346 (2004). The uptake of thiols or disulfides from solution to form self-assembled monolayers (SAMS) on the surface of group 11 metals is of importance in catalysis, biomolecular sensing, and microscopy among other applications. The formation of thiol SAMS on gold and silver nanoparticles has been applied to form colloids as well as solid phases of cross-linked particles. See Brust, M., et al., *Colloids and Surfaces, A: Physicochemical and Engineering Aspects,* 202(2-3): 175-186 (2002) and Daniel, M.-C., et al., *Chemical Reviews (Washington D.C.),* 104(1): 293-346 (2004). In recent years, the solubility properties and methods for their manipulation have been detailed for these colloids. The potential of metal colloids for diagnostics and therapeutics has been recently mentioned. See Paciotti, G. F., et al., *Drug Delivery,* 11(3): 169-183 (2004); U.S. Patent Publication 20050175584; U.S. Patent Publication 20020192814; and Visaria, R. K., et al., *Molecular Cancer Therapeutics,* 5(4): 1014-1020 (2006).

Thiol (R—SH) and disulfide (R—SS—R) groups on compounds are employed to attach said compounds to metal and metal oxide surfaces. Those surfaces may be but are not limited to Ag, Au, Cu, Fe, FeO, $Fe_2O_3$, and $Fe_3O_4$. When thiols are employed as the attaching groups the attachment to metal may not be the sole reaction that occurs as thiols readily oxidize to form disulfide groups. The oxidation to form disulfide groups is undesirable when it results in the polymerization of the organic compounds that would otherwise attach to a metal surface to form a self-assembled monolayer (SAM). The polymerization of S—R—S groups results in a construct whose properties as a solute and as a contrast agent are difficult to control. Prior art shows that the complex [Gd (DTPA) dithiol] on a metal (M) particle forms a multilayer. See Debouttiere et al., *Advanced Functional Materials,* 16(18): 2330-2339 (2006).

The present invention is directed to overcoming these and other deficiencies in the art.

SUMMARY OF THE INVENTION

One aspect of the present invention is directed toward a multivalent product. This product includes a nanoparticle with a metal, metal alloy, or metal oxide core. A plurality of non-polymerizing ligands are bound to the nanoparticle, and a plurality of paramagnetic ions are coupled to the nanoparticle by the ligands.

Another aspect of the present invention is directed to a method of making the multivalent product. This method includes providing a non-polymerizing ligand and a paramagnetic ion. The ligand and the paramagnetic ion are contacted under conditions effective to form a paramagnetic ion-ligand complex. A solution of nanoparticles with a metal, metal alloy, or metal oxide core is provided and contacted with the paramagnetic ion-ligand complex under conditions effective to form the multivalent product.

A further aspect of the present invention is directed toward a method of imaging. This method includes providing the multivalent product and a subject to be imaged. The multivalent product and the subject are contacted, and the subject is imaged using the multivalent product. The present invention is useful in providing targeting and imaging capabilities in the treatment of tumors and other abnormalities of tissue. The construct is designed to consist of a monolayer of metal complexes on a metal core. The monolayer is achieved by the attachment of complexes with thiol or disulfide groups to the metal surface. The complexes incorporate thiols and disulfides that are contacted with a metal surface in a solution under dialysis. As a result, excess complex is removed thereby preventing the formation of disulfide bonds to excess complexes and the resultant formation of multilayers on the metal surface. The complex is also formed from complexes that contain intramolecular disulfide bonds and are designed against the formation of intermolecular disulfide bonds which can lead to multilayer formation. The formation of a monolayer of complexes on the metal core provides uniformity in the chemical and physical properties of the construct that are important to its targeting and imaging characteristics.

In one embodiment of the present invention, the construct has a metal core that is over layered with metal ion complexes. Metal ion complexation can take place on the metal core or in solution following which the metal ion complex can be attached to the metal core. Metal ion complexation on the metal core ensures the formation of monolayer of metal ion complexes in solution. The complexes described can be readily modified to incorporate diverse chemical groups to allow targeting, imaging, and evasion of the immune system.

BRIEF DESCRIPTION OF THE DRAWINGS

FIG. 3A is the highest concentration; FIG. 3B is diluted by a factor of 10; FIG. 3C is diluted by a factor of 20; and FIG. 3D is diluted by a factor of 40.

FIG. 6A shows the aliphatic region of Compound 2, and FIG. 6B shows the aliphatic region of Construct 6, in $D_2O$.

FIG. 7A shows the carbonyl region of Compound 2, and FIG. 7B shows the carbonyl region of Construct 6, in $D_2O$.

DETAILED DESCRIPTION OF THE INVENTION

One aspect of the present invention is directed toward a multivalent product. This product includes a nanoparticle with a metal, metal alloy, or metal oxide core. A plurality of non-polymerizing ligands are bound to the nanoparticle, and a plurality of paramagnetic ions are coupled to the nanoparticle by the ligands.

The nanoparticle may have a shape which is spherical, rod shaped, or polyhedral. The metal in the nanoparticle may be selected from the group consisting of gold, silver, copper, platinum, iron, and mixtures thereof. The iron may be present in the nanoparticle as an iron oxide selected from the group consisting of FeO, $Fe_2O_3$, $Fe_3O_4$, and mixtures thereof.

The paramagnetic ions may be selected from ions of the lanthanide series, ions of the transition metal series, and mixtures thereof. Suitable lanthanides or transition metal ions include ions of iron, gadolinium, europium, manganese, dysprosium, ytterbium, lanthanum, lutetium, and mixtures thereof.

Figure 24:
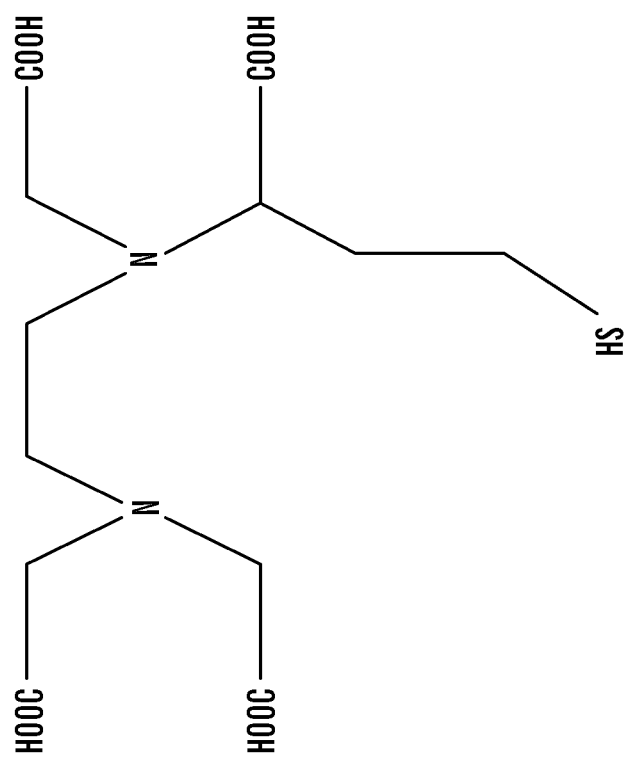
FIG. 24 shows the structure of 2,2'-((2-((1-carboxy-3-mercaptopropyl)(carboxymethyl)amino)ethyl)azanediyl)diacetic acid.
Figure 25:
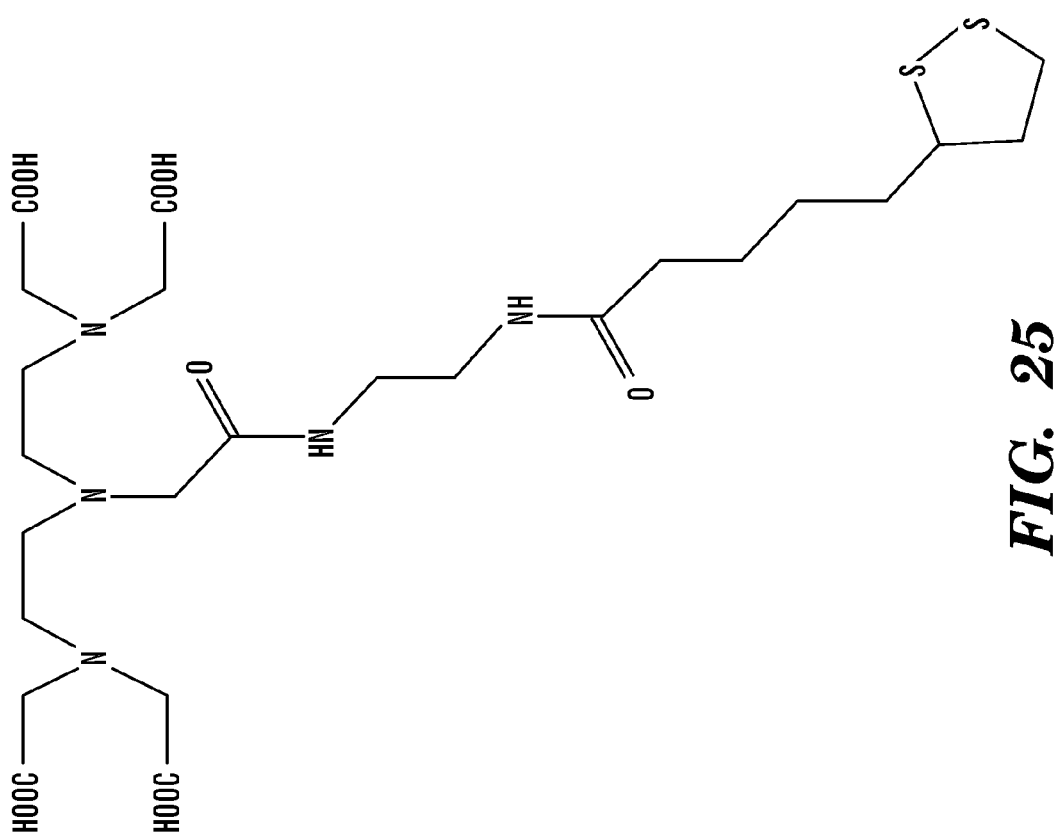
FIG. 25 shows the structure of 5-(2-(bis(carboxymethyl)amino)ethyl)-2-(carboxymethyl)-16-(1,2-dithiolan-3-yl)-7,12-dioxo-2,5,8,11-tetraazahexadecane-1-carboxylic acid.
Figure 26:
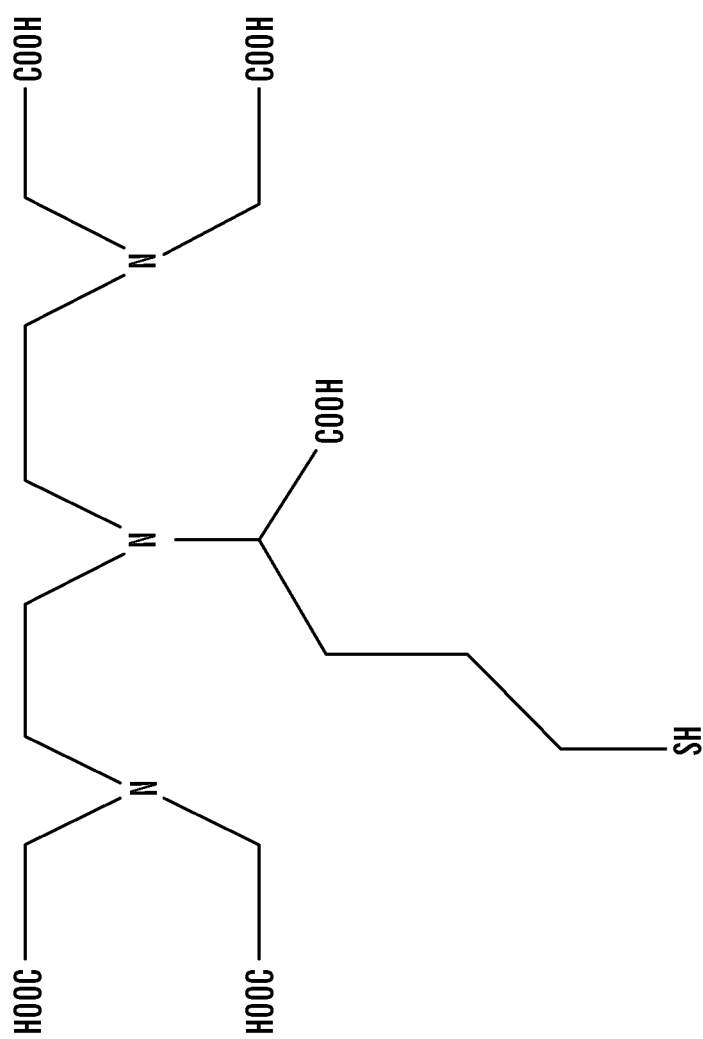
FIG. 26 shows the structure of 2,2',2'',2'''-((((1-carboxy-4-mercaptobutyl)azanediyl)bis(ethane-2,1-diyl))bis(azanetriyl))tetraacetic acid.

The ligands may be cysteine N,N'-tetraacetic acid, diethylenetriaminepentaacetic acid-L-Cys, diethylenetriaminepentaacetic acid lipoic acid, 1,4,7,10-tetracarboxymethyl-1, 4,7,10-tetraazacyclododecane-L-Cys, 1,4,7,10-tetracarboxymethyl-1,4,7,10-tetraazacyclododecane-lipoic acid, 2,2'-((2-((1-carboxy-3-mercaptopropyl)(carboxymethyl)amino)ethyl)azanediyl)diacetic acid (FIG. 24), 5-(2-(bis(carboxymethyl)amino)ethyl)-2-(carboxymethyl)-16-(1,2-dithiolan-3-yl)-7,12-dioxo-2,5,8,11-tetraazahexadecane-1-carboxylic acid (FIG. 25), 2,2',2'',2'''-((((1-carboxyl-4-mercaptobutyl)azanediyl)bis(ethane-2,1-diyl))bis(azanetriyl))tetraacetic acid (FIG. 26), and mixtures thereof.

The product may also include a plurality of polyethylene glycol (PEG) molecules attached to the nanoparticle. The PEG groups form a corona around the metal core. The PEG corona prevents particle aggregation prior to administration to a subject and renders the particle largely undetectable by the reticuloendothelial system after administration. Such particles are long-circulating in the blood stream, which can reduce the amount to be injected, extend the duration of MRI data acquisition, and provide more detailed images.

The product may also include a plurality of alkane thiol or disulfide containing molecules attached to the nanoparticle. The attachment of alkane thiols is useful for adjusting the concentration of lanthanide complexes on the particle surface. The addition of alkane thiols also permits control of the solubility of the particle. Simple alkane thiols lower the solubility of the particles (constructs). Complex alkane thiols such as polyethylene glycol thiols increase the water solubility of the constructs and enhance their evasion of the immune (reticuloendothelial) system. That evasion allows the constructs to persist in the circulatory system thereby enhancing tissue targeting and image construction.

The product may also include a plurality of peptides containing cysteine attached to the particle. Peptides serve to alter the targeting properties and solubility of the construct. The product may also include a plurality of radioisotopes attached to the particle. Radioisotopes allow, for example, monitoring of delivery of the particles as well as delivery of drugs or other molecules through the targeted constructs such as peptides.

In another embodiment the particles, comprised of a metal or metal oxide core with gadolinium or manganese complexes attached to the surface, are prepared in micelles consisting of amphiphilic surfactants such as, but not limited to, diblock- and triblock poloxamers such as the Pluronic F 127, F 108, and P 85. These poloxamers have the structure $PEO_x$-$PPO_y$-$PEO_x$, $-HO(C_2H_4O)_x(C_3H_6O)_y(C2F14O)_xH$ where PEO is polyethylene oxide, and PPO is polypropylene oxide, and x=101 and y=56 for Pluronic F 127. The poloxamers assemble to form micelles in aqueous medium with a hydrophobic core formed by the association of PPO oligomeric blocks, and a hydrophilic corona comprised of PEO oligomeric blocks.

Another aspect of the present invention is directed to a method of making the multivalent product. This method includes providing a non-polymerizing ligand and a paramagnetic ion. The ligand and the paramagnetic ion are contacted under conditions effective to form a paramagnetic ion-ligand complex. A solution of nanoparticles with a metal, metal alloy, or metal oxide core is provided and contacted with the paramagnetic ion-ligand complex under conditions effective to form the multivalent product. The specific materials used to form the multivalent product as well as the shapes and structures of the product are substantially the same as those described above.

A further aspect of the present invention is directed toward a method of imaging. This method includes providing the multivalent product and a subject to be imaged. The multivalent product and the subject are contacted, and the subject is imaged using the multivalent product.

The method of imaging may include magnetic resonance imaging (MRI), fluorescence imaging, surfaced-enhanced Raman imaging, radiologic imaging, or the targeted delivery of radioisotopes. The targeted delivery of radioisotopes may include targeted delivery of radioisotopes to tissues such as tumors.

The method of imaging may include imaging carried out in conjunction with a real-time MRI or CT guided procedure. The MRI guided procedure may be a surgical procedure, such as balloon angioplasty or catheterization.

EXAMPLES

Example 1

Materials

All chemicals were used as received without further purification. $^{13}C$ and $^1H$ nuclear magnetic resonance spectroscopy were performed on a Bruker Avance 400 MHz NMR instrument. Dialyses were carried out using cellulose tubes with 1200 molecular weight cut off. Thermogravimetric analyses on dried powders of nanoparticles (10-15 mg) were carried out on a Texas Instruments SDT Q600. Profiles were acquired by using a Universal Analysis program. Electrospray data were obtained on an Agilent 1100 Series Capillary LCMSD Trap XCT instrument. Infrared data was obtained on Nicolet 750 spectrometer. TEM images were obtained on carbon coated copper grids and examined under a Philips CM-12 electron microscope. Photographs were taken by a Gatan 1 k×1 k digital camera.

Example 2

Synthesis of Diethylenetriamine-1,1',4,7,7'-pentacetic Acid (DTPA)-1,7-bis Anhydride (1)

DTPA 6.0 g (15.33 mmol) was suspended in 27 mL of 5:4 (v/v) pyridine and acetic anhydride. The solution was gradually heated to 60° C.-65° C. and stirred under inert atmosphere for 24 hr. The product was collected by filtration washed with acetonitrile followed by ether and dried under vacuum. This produced a fine yellow powder with 94% yield. See Jasanada, F., et al., *Tetrahedron Lett.*, 33(39): 5745-5748 (1992), which is hereby incorporated by reference in its entirety.

Example 3

Synthesis of DTPA-L-Cysteine (2)

L-Cysteine 1.76 g (11.19 mmol) was deprotonated in 100 ml water with equimolar amount of $Na_2CO_3$ 0.59 g (5.59 mmol). To this solution, compound 1, 2.0 g (5.59 mmol) was added, and the solution was stirred at rt for 24 h. The water was removed under vacuum and methanol was added. The insoluble salts were removed from the methanol solution by filtration. The methanol was then removed under vacuum and replaced by acetone. Acetone was added to the solid to extract residual water and methanol. The product was collected by filtration and dried under vacuum leaving a yellow powder. Yield 93.3%

Example 4

Synthesis of GdDTPA-L-Cysteine (3)

Compound 20.25 g (0.418 mmol) was dissolved in 30 mL of water. To this solution $Gd_2O_3$ 75.8 mg (0.209 mmol) was added and refluxed for 4 hr. The $Gd_2O_3$ was not fully soluble in water but after the reflux the solution was clear. Water was removed under reduced pressure. Acetone was added to the solid to remove the excess water and make it more like a powder. The resulting yellow powder solid was collected by vacuum filtration and dried under vacuum with 82% yield. See Konings, et al., *Inorganic Chemistry*, 29: 1488-1491 (1990), which is hereby incorporated by reference in its entirety.

Example 5

Synthesis of LaDTPA-L-Cysteine (4)

To a solution of compound 20.75 g (1.26 mmol) in 30 mL of water $NaHCO_3$ 0.3176 g (3.78 mmol) was added to deprotonate the ligand. $LaCl_3 \cdot 7H_2O$ 0.531 g (1.38 mmol) was added and the solution was refluxed for 3 hours and then the water was removed under reduced pressure. To the solid, 30 mL of ethanol was added and refluxed for 1 hr. The solid was isolated with vacuum filtration and dried under vacuum.

Example 6

Synthesis of Potassium Cysteine N,N' Tetraacetic Acid (5)

L-cysteine 3.00 g (12.48 mmol) was mixed with 3.9 mL of aqueous KOH (6.4 M, 24.96 mmol). A solution of potassium bromoacetate was prepared from 12.68 mL of aqueous KOH (6.4 M, 81.15 mmol) and 11.28 g of bromoacetic acid (81.15 mmol) and allowed to cool to room temperature. It was then added to the L-cysteine solution. 12.68 mL of aqueous KOH was then added to the mixture (6.4 M, 81.15 mmol). The resulting solution was slightly yellow and contained a small amount of undissolved L-cysteine. The reaction vessel was allowed to sit for three days. The product, $K_4H_2CNTA$, and the reaction byproduct, KBr, were precipitated from solution by the addition of approximately 350 mL of methanol. The solid was allowed to settle overnight. The crude product was collected by filtration and purified by Soxhelet extraction with methanol for 24 hours. The product was collected and dried under vacuum with 48.6% yield.

Example 7

Preparation of Surface Derivatized Silver Nanoparticles for $^1$H and $^{13}$C NMR The silver particles were prepared using the method of Joo. See Joo, T., et al., *Chemical Physics Letters*, 112 (1): 65-68 (1984), which is hereby incorporated by reference in its entirety. Aqueous $AgNO_3$ 10 mL (0.001M, 0.01 mmol) was added to aqueous $NaBH_4$ 30 mL (0.002 M, 0.06 mmol) over ice with stirring. The resulting yellow/brown light sensitive solution containing silver nanoparticles was handled in a light shielding reaction vessel and with minimal exposure to light in the succeeding steps. To this solution 0.01 mmol of ligand (R), where R=2, 3, 4, or 5, was added with stirring. The mixture was allowed to stir for 30 minutes. The solution was concentrated to approximately 5.0 mL by rotary evaporation, and the sample was dialyzed against distilled water overnight. The dialyzed sample was dried by rotary evaporation and the dark solid was resuspended in 1.0 mL of $D_2O$ for $^1$H NMR analysis.

Example 8

Preparation of Surface Derivatized Silver Nanoparticles for TGA and $T_1$ Studies Samples of Ag-DTPA-L-Cysteine (6), Ag—GdDTPA-L-Cysteine (7), Ag—LaDTPA-L-Cys (8), and Ag-Cysteine N,N' tetraacetic acid (9) were prepared as above with all concentrations scaled up by ten. The solutions were concentrated to approximately 5.0 mL by rotary evaporation, and each was dialyzed against distilled water overnight. The dialyzed solutions were lyophilized to dryness and dark brown/black solids were collected. Thermogravimetric analyses (TGA) were performed on approximately 10-15 mg of the obtained solids. $T^1$ studies were performed with solutions of various concentrations of 7.

Example 9

Preparation of Ag—LaCNTA (10) for $^1$H and $^{13}$C NMR

Lanthanum chloride, $LaCl_3.7H_2O$ (2.45 mg, 0.01 mmol) was added to a 40 mL solution of 8 with stirring to form the diamagnetic analog of the paramagnetic complex of 5. A slightly brown, clear solution was obtained after stirring overnight. The solution was concentrated to approximately 5 mL by rotary evaporation and was dialyzed against distilled water overnight. The dialyzed sample was then dried under vacuum and the resulting dark solid was redissolved in 0.5 mL of $D_2O$.

Example 10

Preparation of Ag—GdCNTA (11) for TGA and $T_1$ Studies

Gadolinium chloride, $GdCl_3.6H_2O$ (38.3 mg, 0.1 mmol) was added to a 40 mL solution of 8 with stirring. A slightly brown/black solution was obtained after stirring overnight. The solution was concentrated to approximately 5 mL by rotary evaporation and the sample was dialyzed against distilled water overnight. The dialyzed solution was lyophilized and a dark brown/black solid was collected. TGA was performed on approximately 10-15 mg aliquots of sample. See Joo, T., et al., *Chemical Physics Letters*, 112 (1): 65-68 (1984), which is hereby incorporated by reference in its entirety. $T_1$ studies were performed with solutions of various concentrations of 11.

Example 11

DTPA-L-Cysteine Characterization

Figure 1:
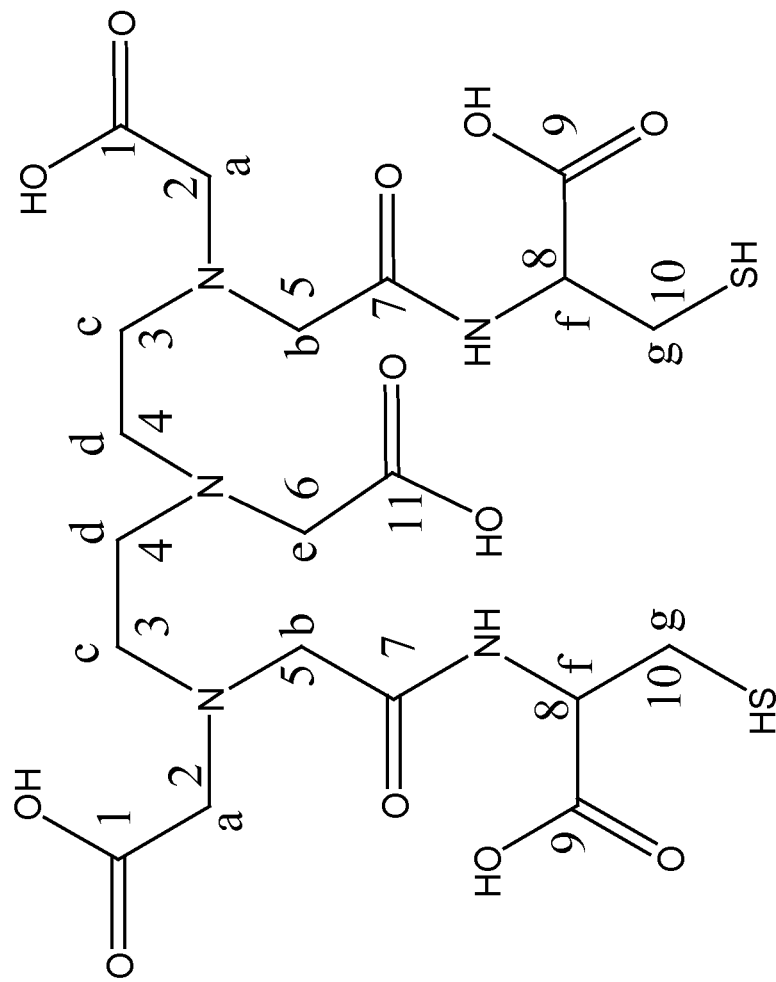
FIG. 1 shows the structure of DTPA-L-Cysteine, the neutral form of Compound 2.
Figure 2:
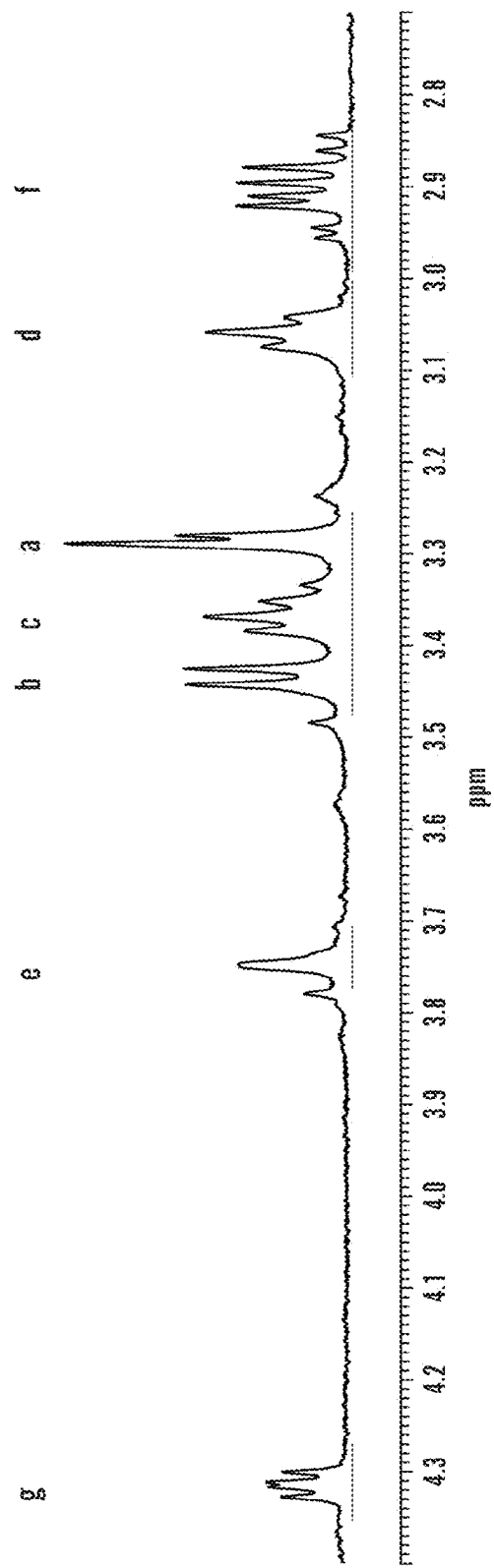
FIG. 2 shows a $^1$H NMR spectrum of Compound 2 in $D_2O$. 2.95 ppm multiplet 4H f, 3.10 ppm triplet 4H d, 3.32 ppm doublet 4H a, 3.4 ppm triplet 4H c, 3.47 ppm doublet 4H b, 3.78 ppm singlet 2H e, 4.35 ppm triplet 2H g.
Figure 3A:
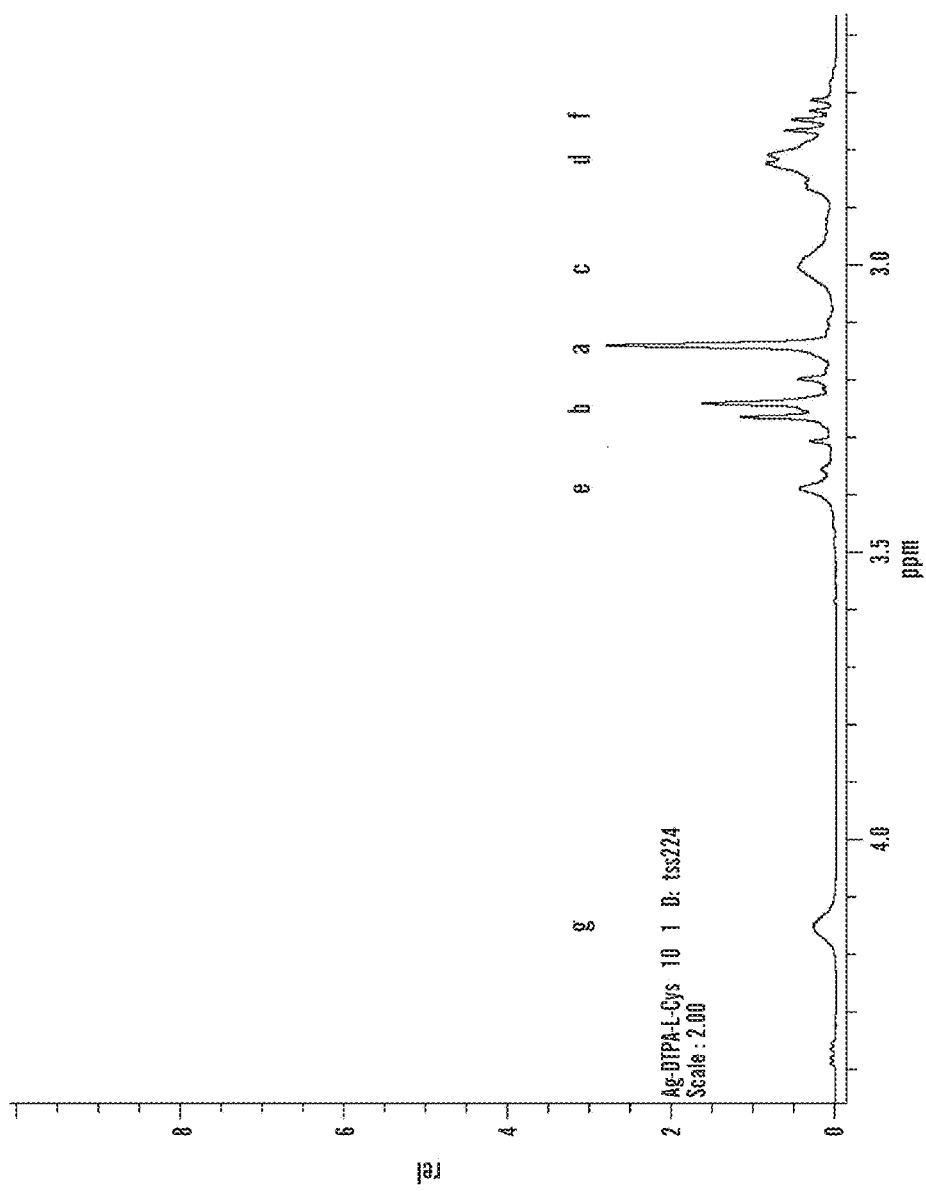
FIGS. 3A-D show $^1$H NMR spectrum of Construct 6 in $D_2O$.
Figure 3B:
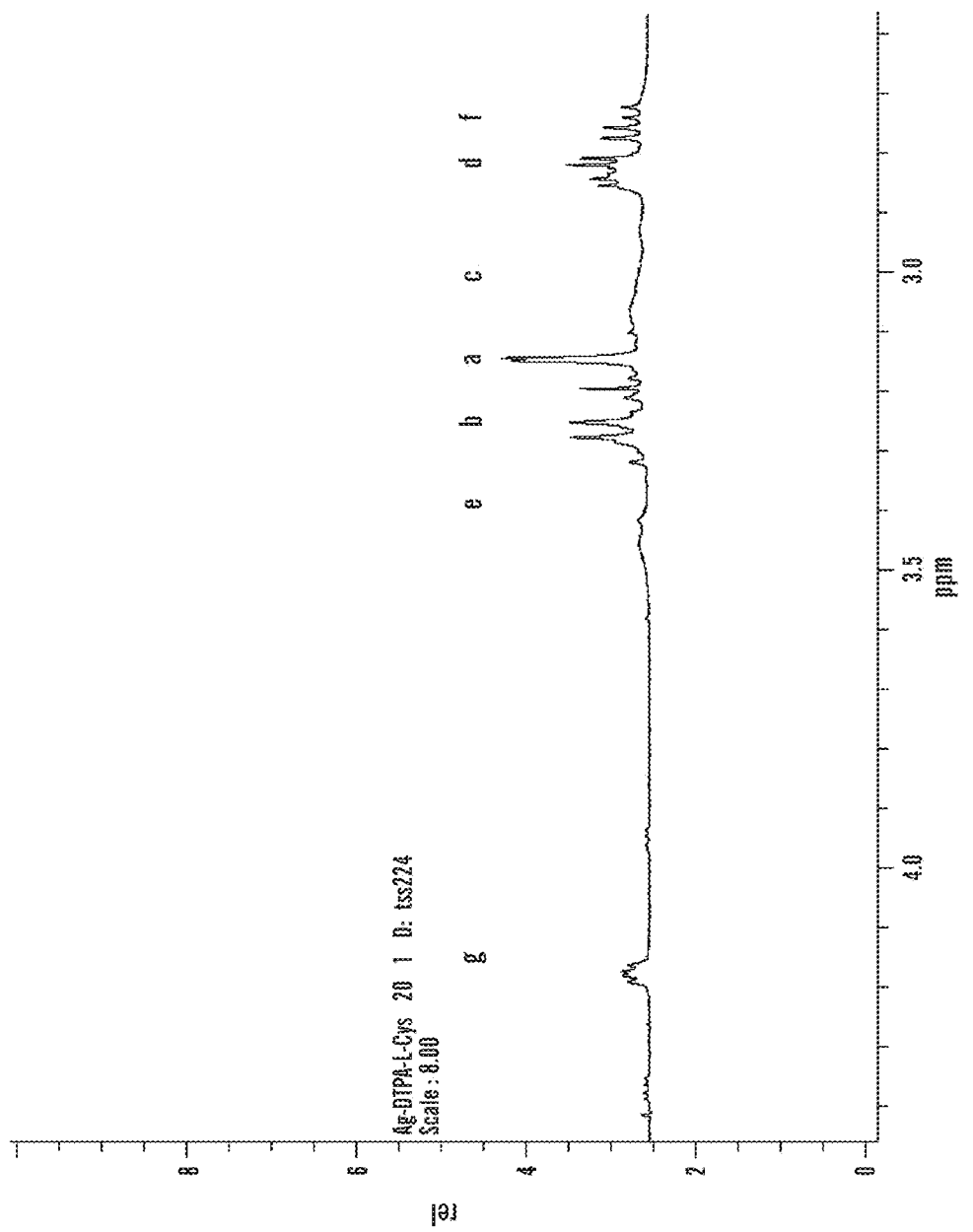
Figure 3C:
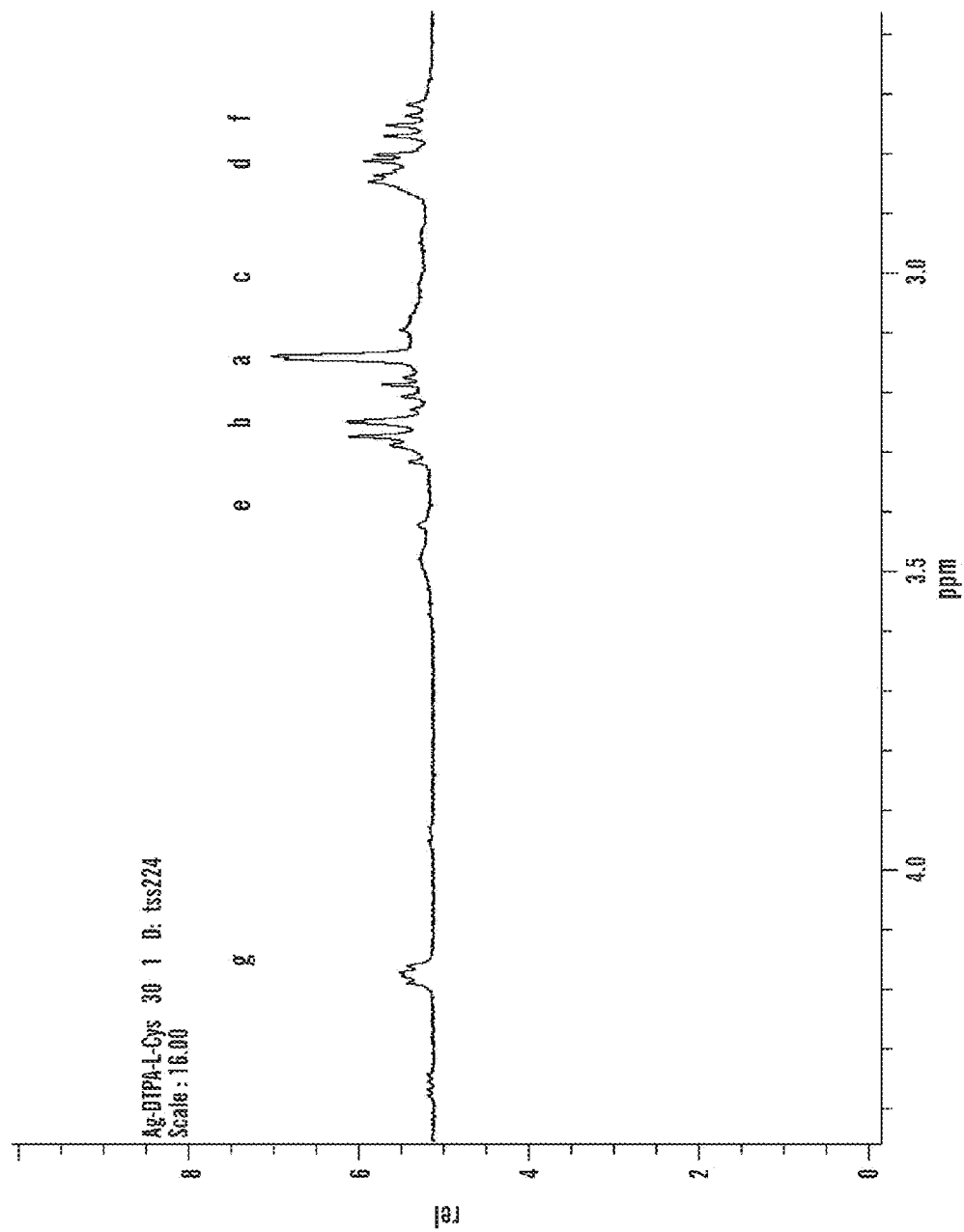
Figure 3D:
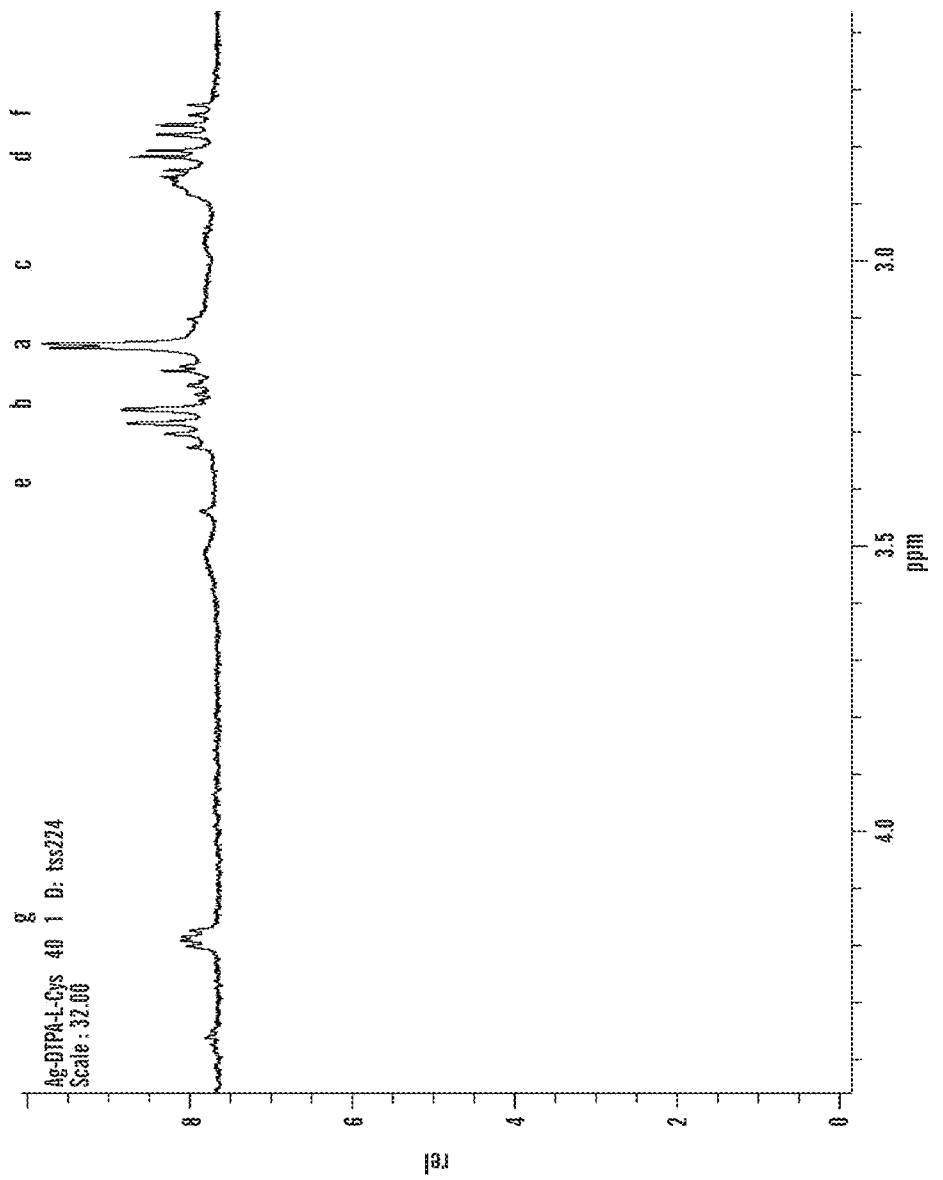
Figure 4:
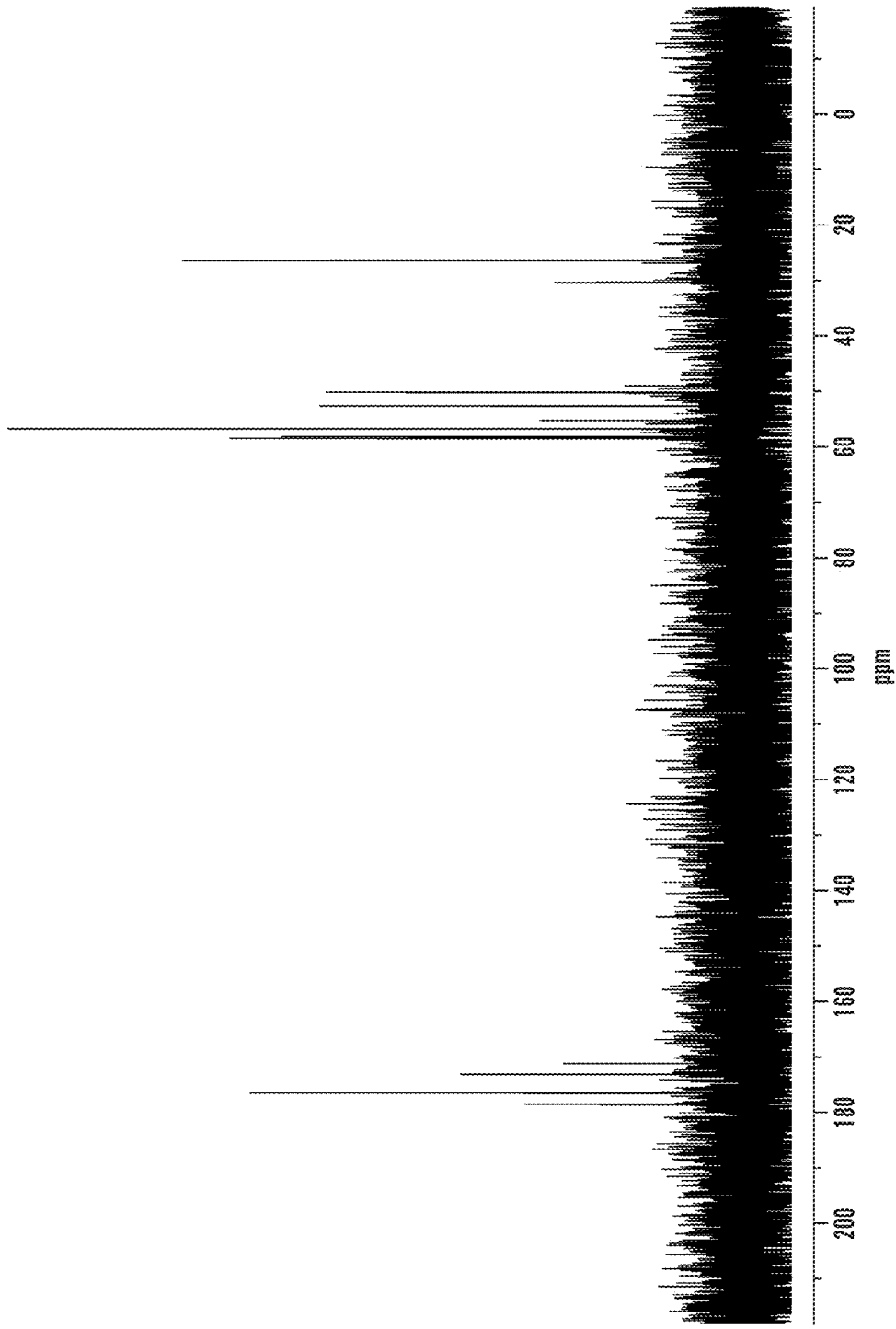
FIG. 4 shows a $^{13}$C NMR spectrum of Compound 2 in $D_2O$. 26.36 (C10), 49.99 (C3), 52.61 (C4), 55.19 (C6), 56.63 (C8), 58.16 (C5), 58.44 (C2), 170.58 (C7), 173.09 (C9), 176.19 (C1), 178.53 (C11). The peak at 30 ppm is acetone.
Figure 8:
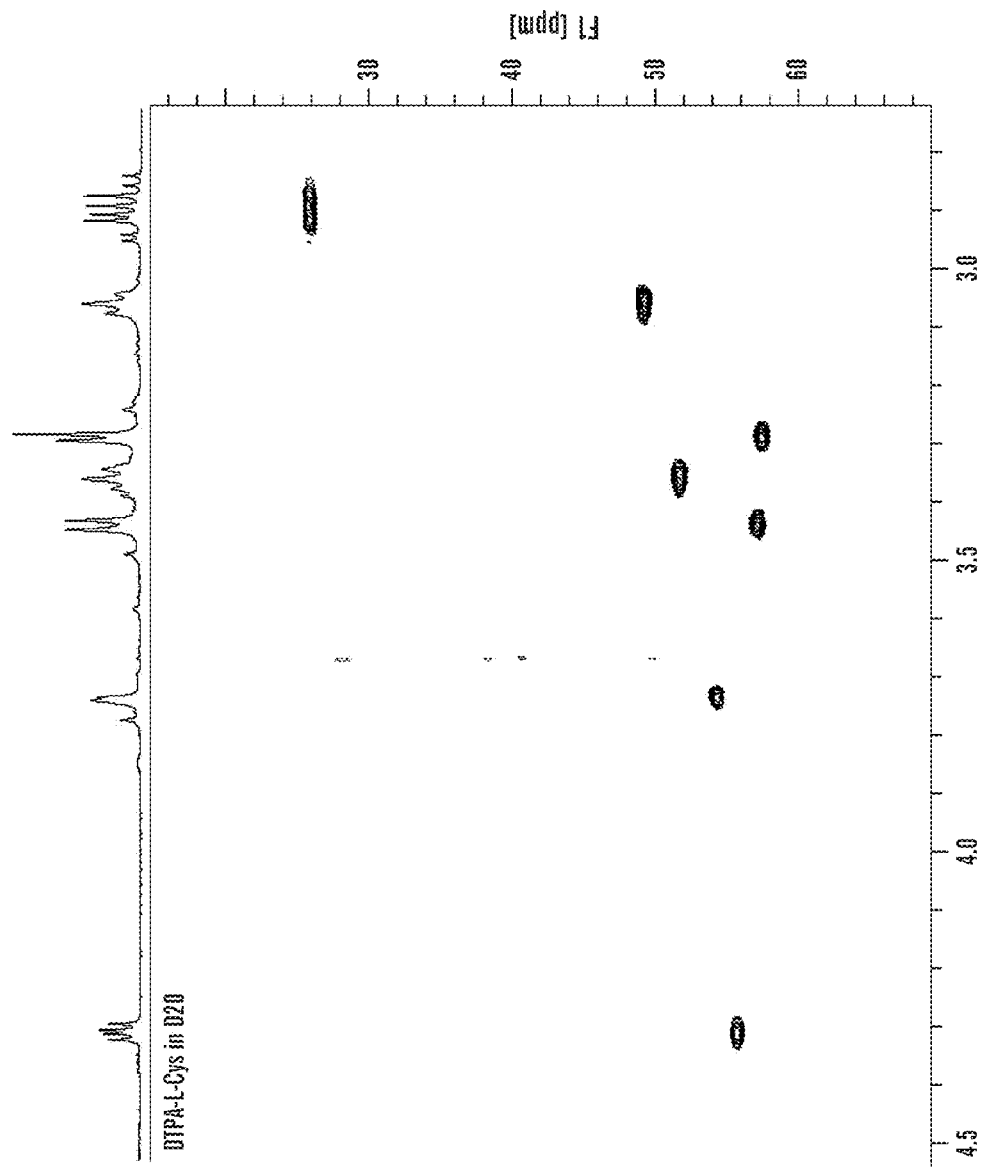
FIG. 8 shows a Heteronuclear Single Quantum Correlation (HSQC) spectrum of Compound 2 in $D_2O$.

Compound 2 (see FIG. 1, DTPA-L-Cysteine, neutral form) was fully characterized by $^1$H NMR (see FIG. 2), $^{13}$C NMR, (see FIG. 4), and assignments were verified by HSQC (see FIG. 8). These spectra were used to characterize functionalized silver nanoparticles, 6 by NMR. FIGS. 3A-D show $^1$H NMR spectra of 6 in a dilution series. The most concentrated sample (see FIG. 3A) exhibited peak broadening that diminished with sample dilution. Overall, the peak correlation was maintained through the dilution series. The spectrum of the most dilute sample (FIG. 3D) correlates well with that of the free ligand (FIG. 2) but for the broadening of peaks assigned to protons c and e (FIG. 2) which is under investigation.

The $^1$H NMR results on Compounds 2 and 6 are in disagreement with results reported by Murray in his study of gold nanoparticles coated with tiopronin. See Kohlmann, O., et al., *Journal of Physical Chemistry B*, 105: 8801-8809 (2001), which is hereby incorporated by reference in its entirety. The Knight effect that was proposed by Murray and coworkers would cause methylene protons in close proximity to a gold (or perhaps silver) metal surface to be shifted downfield and broadened. It is observed that the peaks that are in close proximity to the binding moieties (sulfur and carboxylate) of construct 6, remain sharp and do not shift; whereas, unexpectedly, other protons are shifted and broadened. See Jing, C., et al., *Chemical Physics*, 332: 27-32 (2007), which is hereby incorporated by reference in its entirety. It is plausible that silver nanoparticles of a certain size do not exhibit a Knight effect. The other possibility that could occur is that only one sulfur atom is attached and the other is free and is located far from the metal particle surface. See Debouttiere, P. J., et al., *Advanced Functional Materials*, 16(18): 2330-2339

(2006), which is hereby incorporated by reference in its entirety. The methylene protons adjacent to the free sulfur could give rise to sharp peaks in the proton NMR whereas the methylene protons adjacent to the attached sulfur give a signal that is broadened and indistinguishable from the spectrum baseline.

Figure 5:
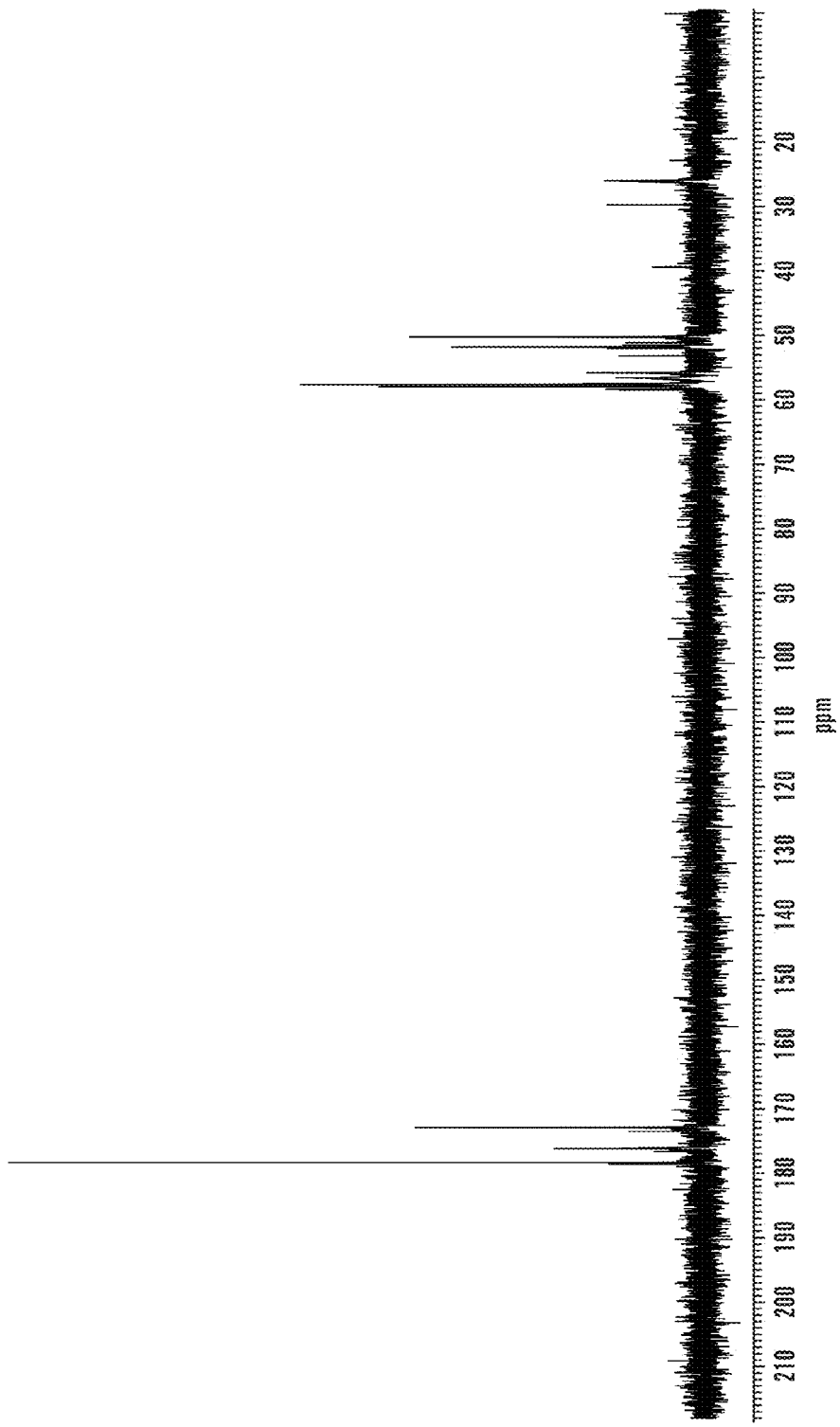
FIG. 5 shows a $^{13}$C NMR spectrum of Construct 6 in $D_2O$.
Figure 6A:
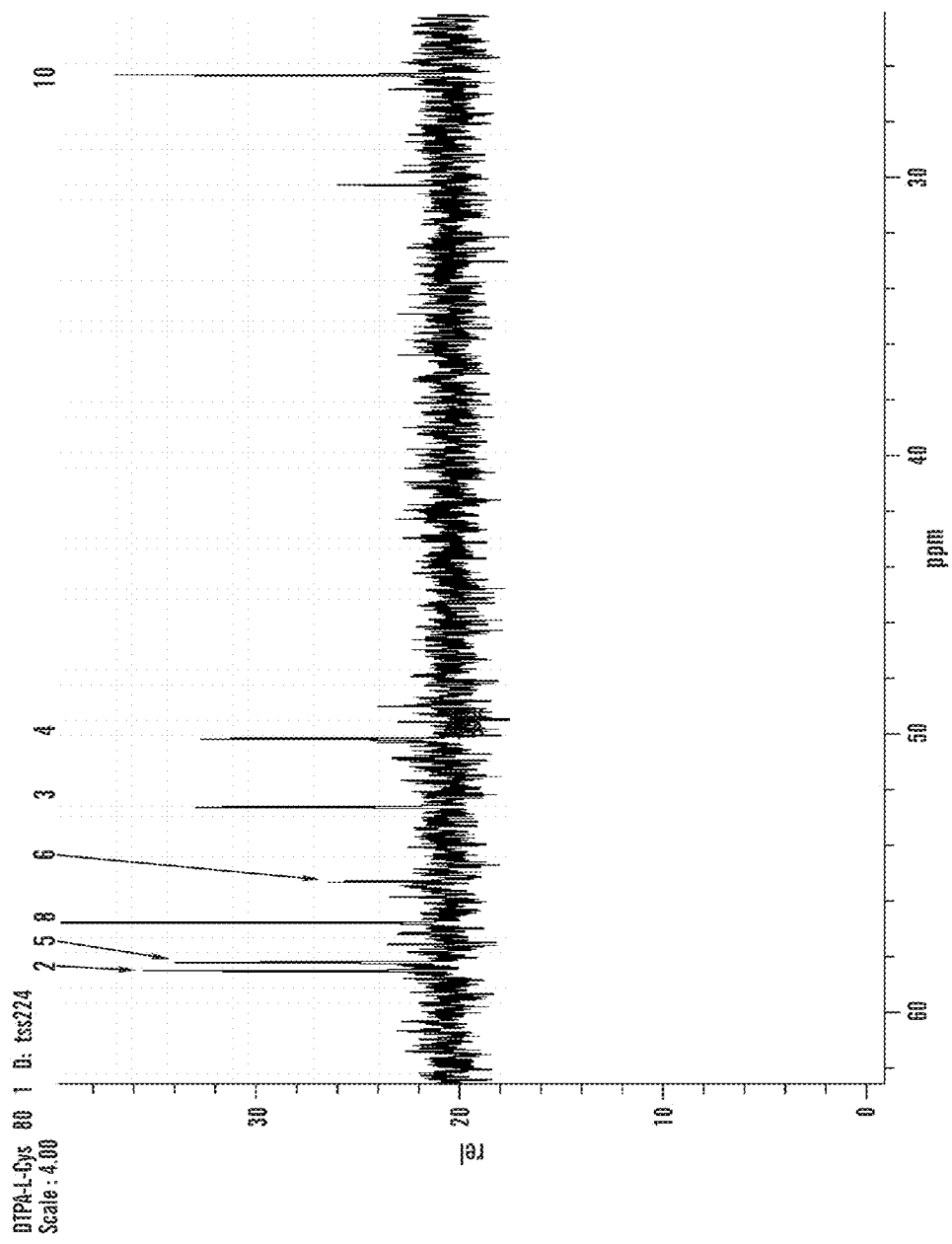
FIGS. 6A-B show $^{13}$C NMR spectra.
Figure 6B:
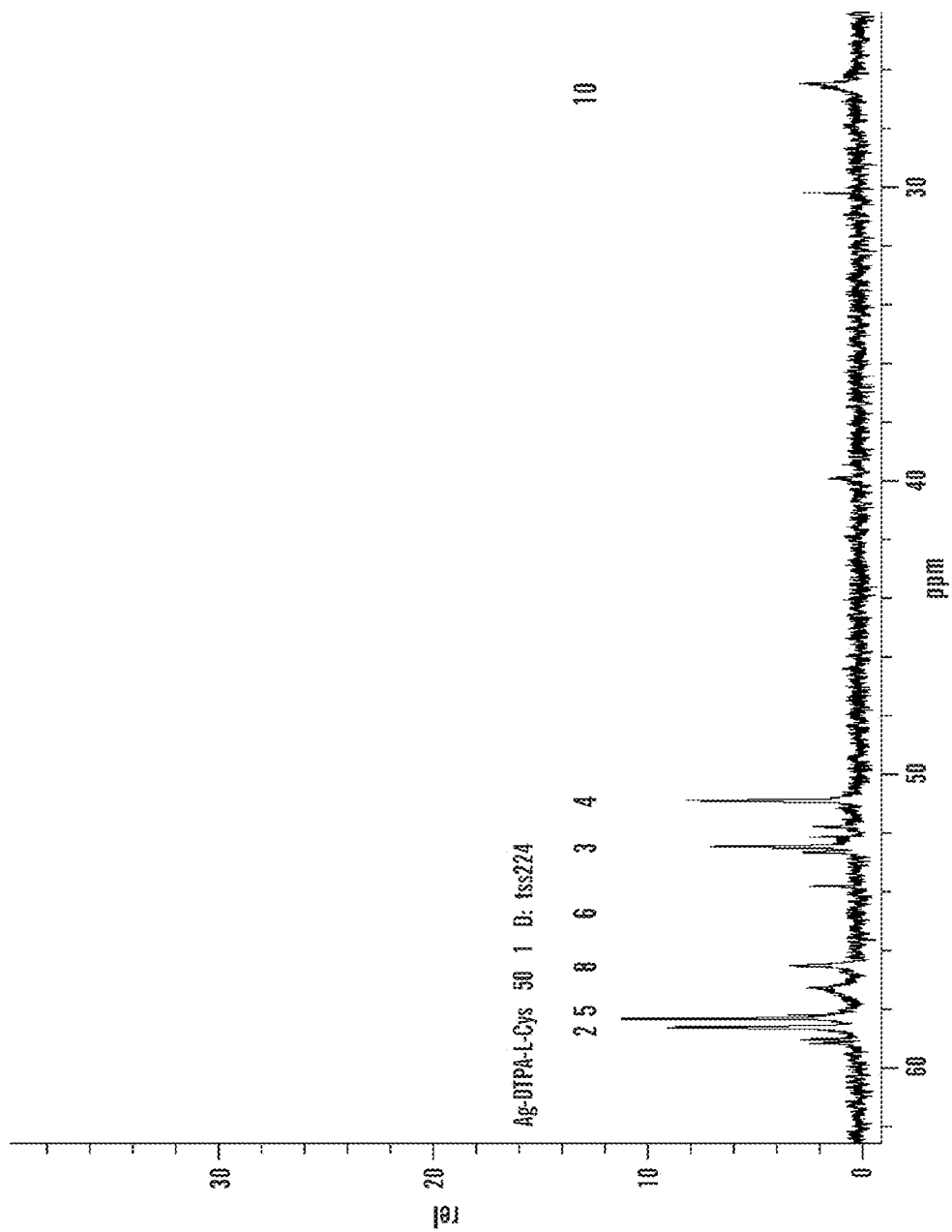
Figure 7A:
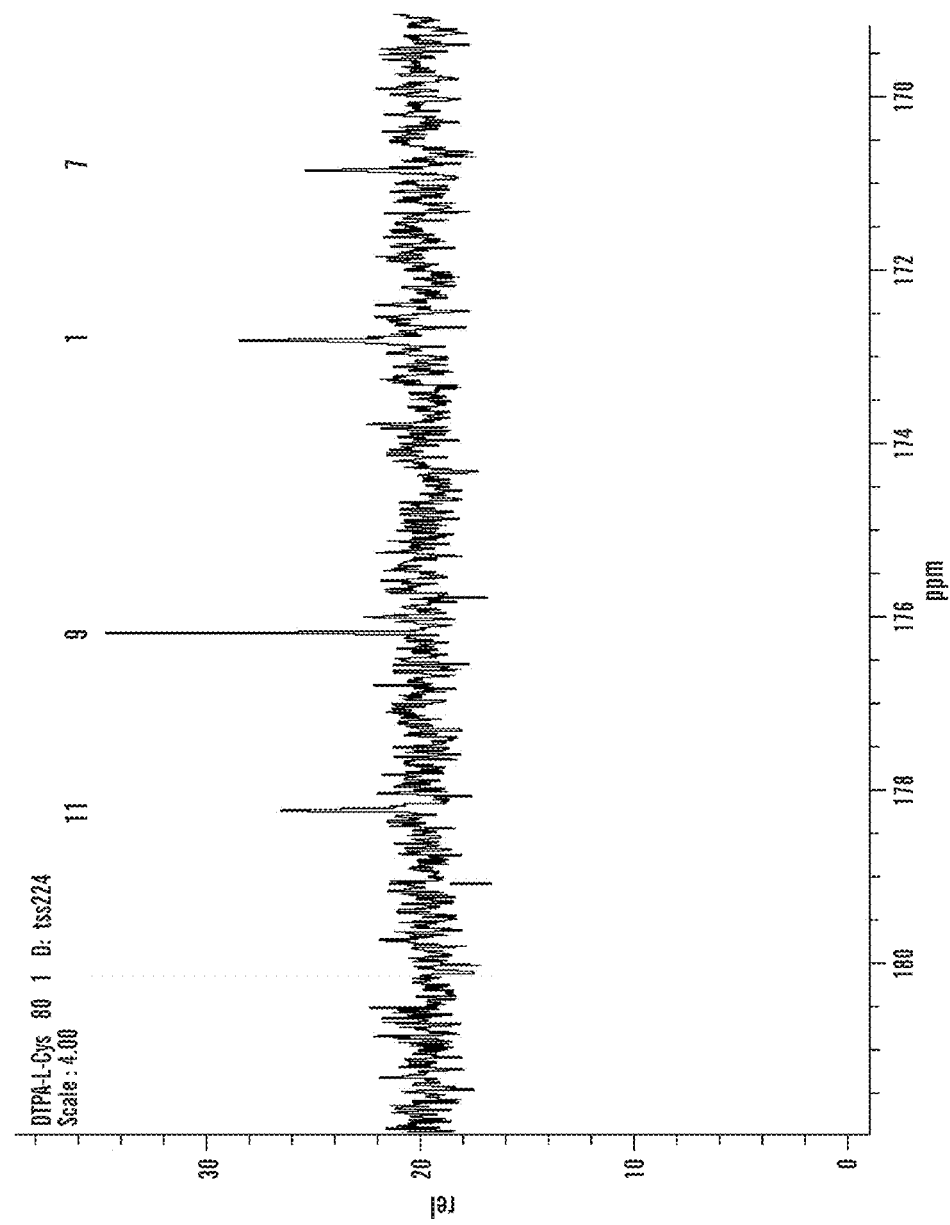
FIGS. 7A-B show $^{13}$C NMR spectra.
Figure 7B:
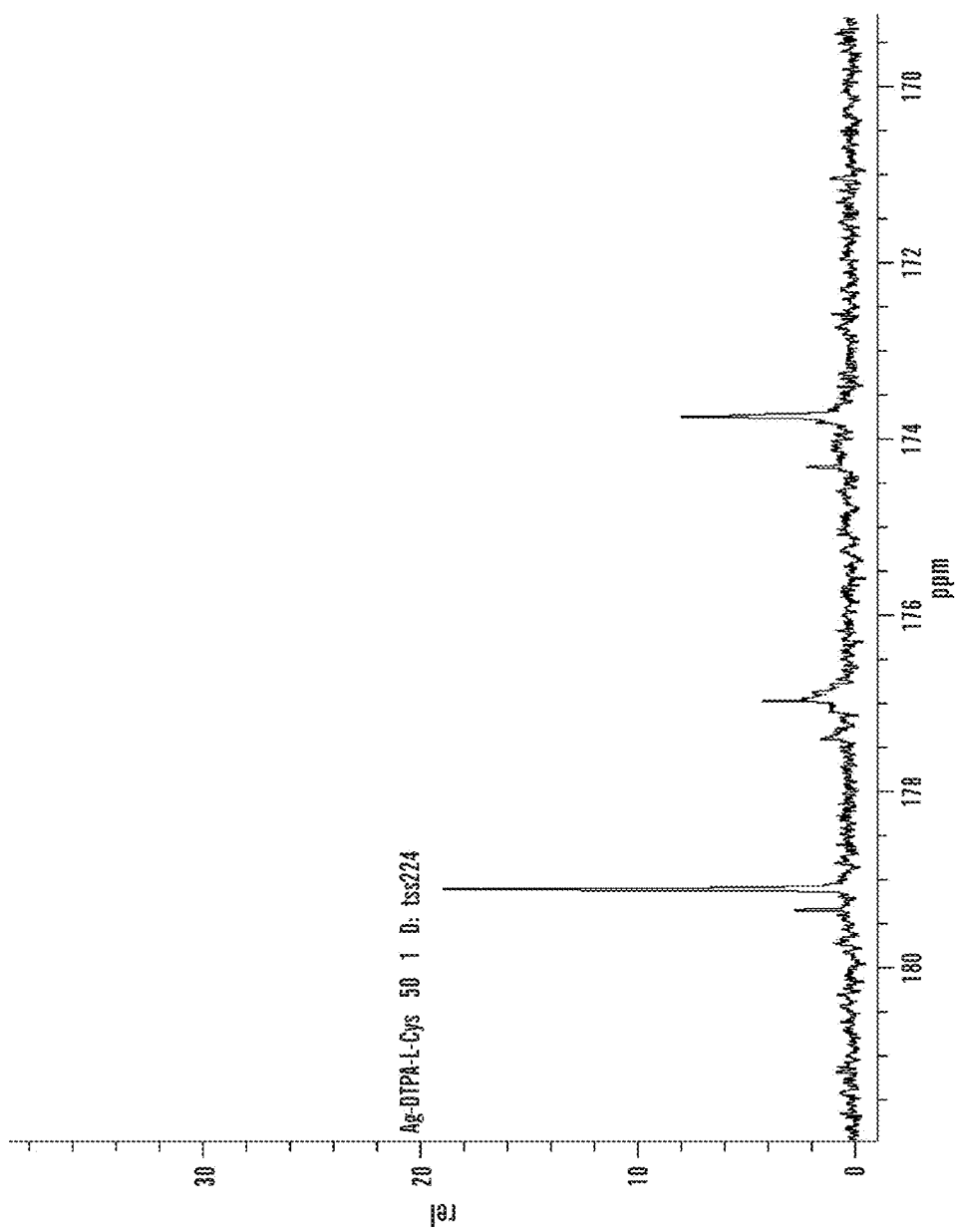

The ligand, 2, was examined through $^{13}$C NMR. See FIG. 4. This spectrum was compared with the $^{13}$C NMR of the silver functionalized particles 6, and significant changes were observed. The first major change, as seen in FIG. 6, is that of the βC on the cysteine group which is next to the sulfur, C10, the peak has decreased and has been broadened. This phenomenon was reported by Murray in his study of alkane capped gold nanoparticles. See Terrill, R. H., et al., *Journal of American Chemical Society*, 117: 12537-12548 (1995), which is hereby incorporated by reference in its entirety. The peaks for carbons close to the sulfur-gold bond were substantially broadened and C1 had been broadened into the baseline. This trend is seen occurring in the $^{13}$C NMR of construct 6 as well. The other site where this broadening is observed to great extent is at αC of the cysteine group, C8. This carbon is two atoms away from the sulfur-gold bond. This peak, as well, was considerably decreased and broadened. The methylene carbon of the middle acetate is shifted and broadened. The other peaks for the aliphatic carbons are only slightly broadened. For the spectra of Construct 6, there are only three major peaks present and all the peaks are shifted with the integration of 1:1:1. See FIG. 5. This suggests that the carboxylate from the middle acetate group is broadened into the baseline. A plausible explanation for the observed broadening is that the middle carboxylate could be attached to the metal particle surface. By examining the $^{13}$C NMR of Construct 6, peaks and the attachment points of the ligand to silver surface can be assigned.

Figure 9:
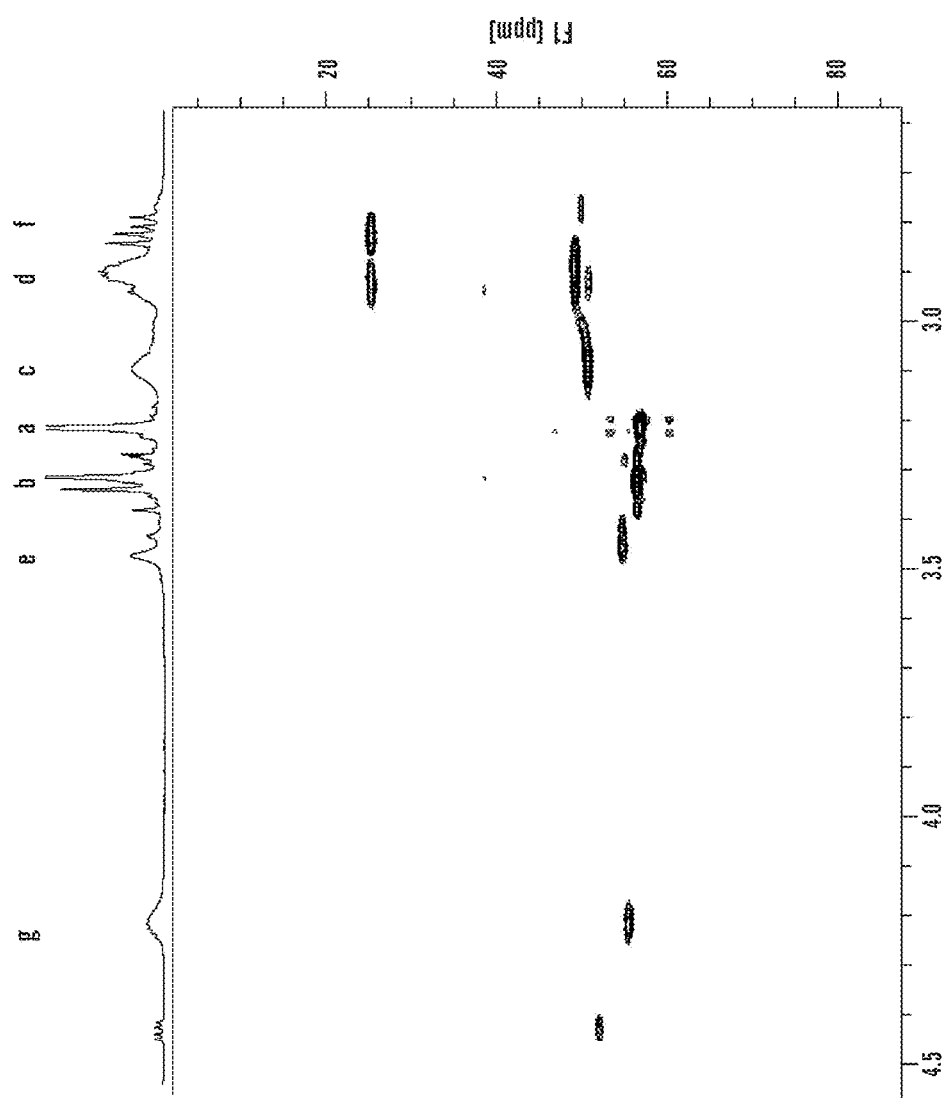
FIG. 9 shows a Heteronuclear Single Quantum Correlation (HSQC) spectrum of Construct 6 in $D_2O$.

The Heteronuclear Single Quantum Correlation (HSQC) data in FIG. 8 for compound 2 has very distinct cross peaks which assisted in the assignment of the $^1$H and $^{13}$C NMR for the compound. HSQC experiment was done for Construct 6 (see FIG. 9), and it is comparable to the HSQC of compound 2. The peaks are elongated which correlates to the broadening of the peaks in the proton spectra. The major difference that is the upfield shift of peak c, which can be due to the structure being locked in a certain environment. The other significant change is that there are two peaks present in for the C10 cross peak. This could be a confirmation of the theory that only one thiol group is attached to the surface and one is free. The one to the right which corresponds to the sharper peak could be for the free thiol and the cross speak to the left could be for the bound sulfur peak which is broadened into the base line.

Example 12

LaDTPA-L-Cys

Figure 10A:
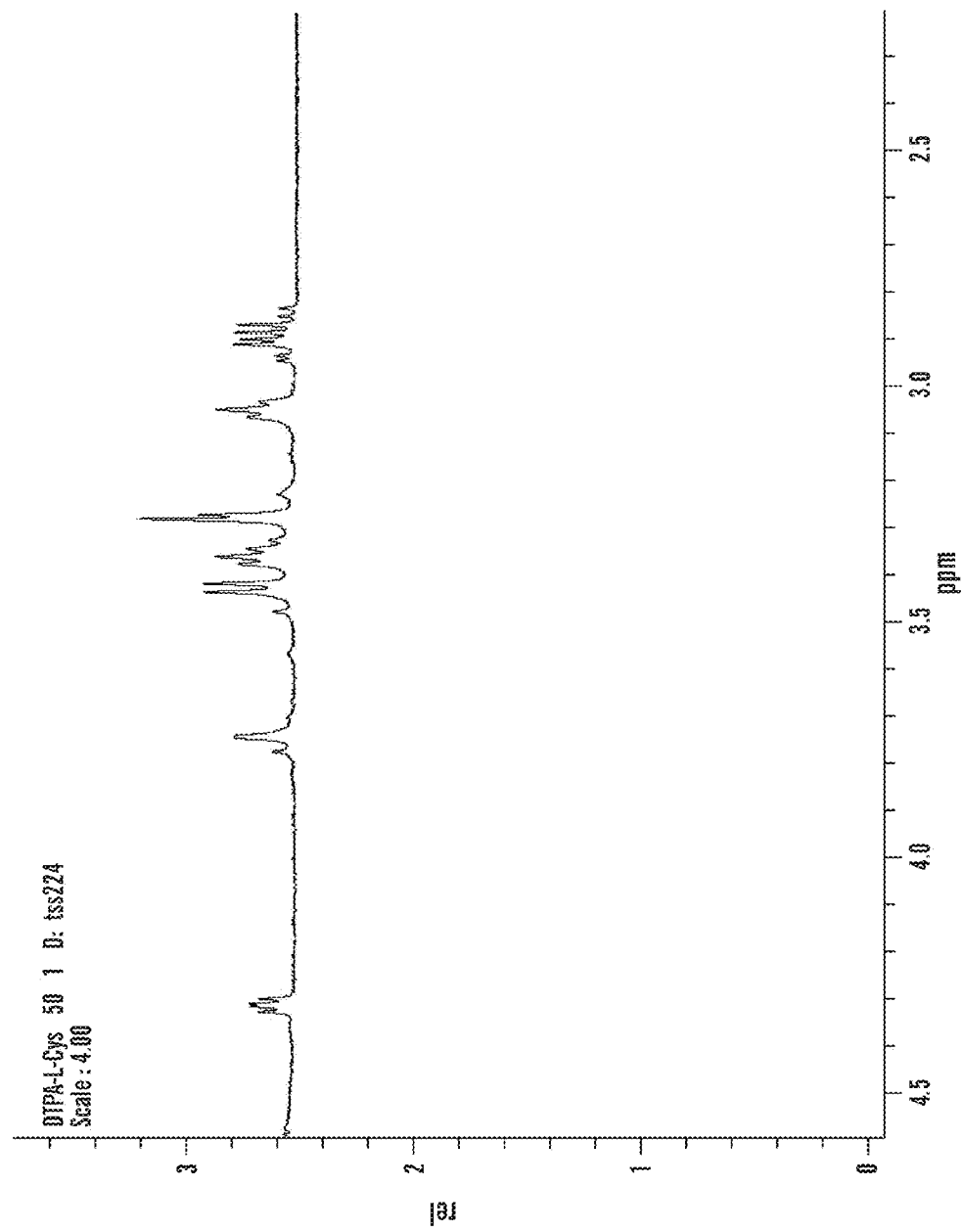
FIGS. 10A-C show $^1$H NMR spectra for Compound 2 (FIG. 10A), Compound 4 (FIG. 10B), and Compound 8 (FIG. 10C), in $D_2O$.
Figure 10B:
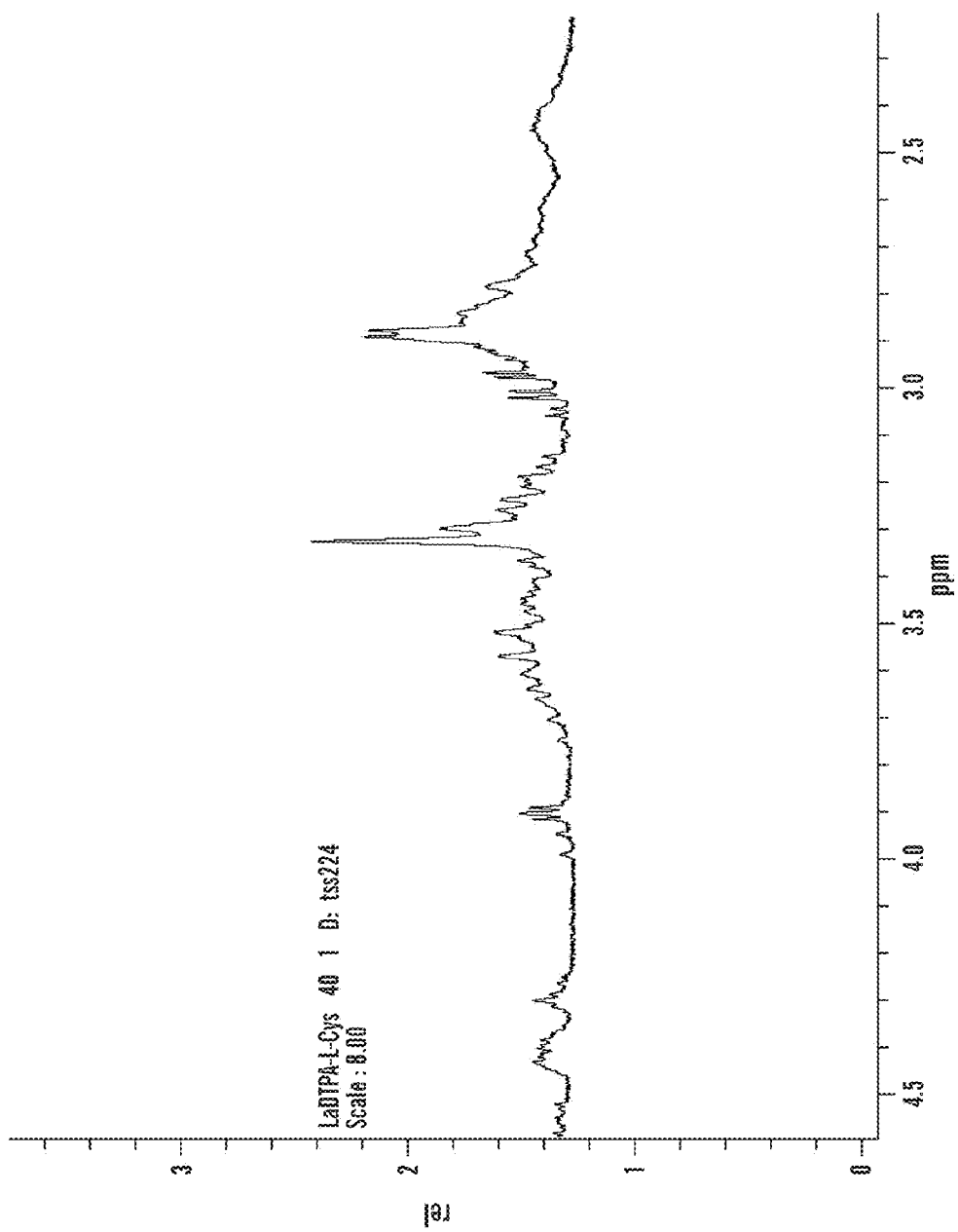
Figure 10C:
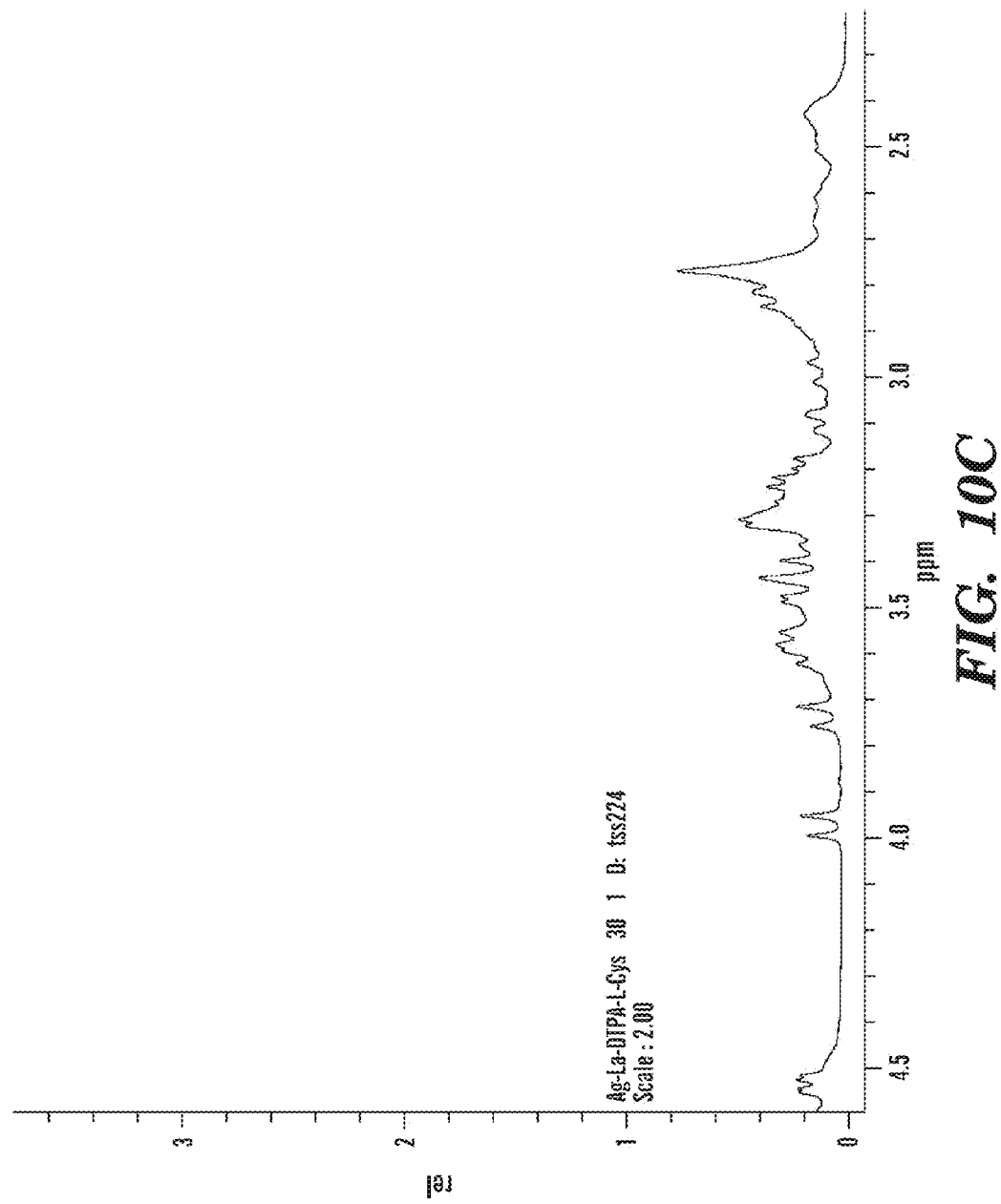
Figure 11:
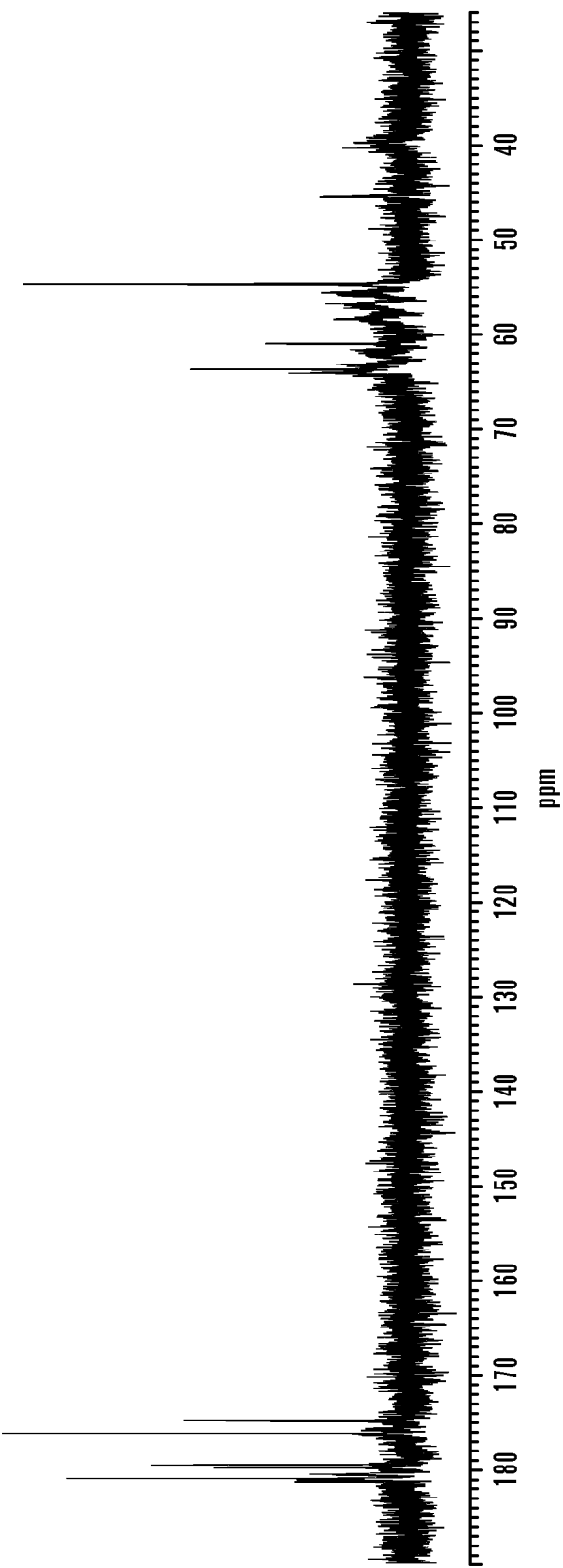
FIG. 11 shows a $^{13}$C NMR spectrum of Compound 8.

Metal complexes of DTPA by NMR have been extensively studied by the Peters. See Geraldes, C. F., et al., *Inorganic Chemistry*, 32: 2426-2432 (1993); Lammers, H., et al., *Inorganica Chimica Acta*, 268: 249-255 (1998); and Lammers, H., et al., *Inorganic Chemistry*, 36: 2527-2538 (1997), which are hereby incorporated by reference in their entirety. Once DTPA binds to lanthanides, it becomes chiral and produces eight enantiomeric complexes with four diastereomeric pairs). When DTPA is converted to a DTPA-bis amide molecule where the group added is chiral, as in compound 2, it doubles the number of diasteromers. See Lammers, H., et al., *Inorganica Chimica Acta*, 268: 249-255 (1998), which is hereby incorporated by reference in its entirety. LnDTPA-bis amide coordination forms polyhedra that are tricapped trigonal prisms that are fluxional in the coordination of lanthanide by the acetate arms of the terminal amine groups. See Geraldes, C. F., et al., *Inorganic Chemistry*, 32: 2426-2432 (1993), which is hereby incorporated by reference in its entirety. At ambient temperature, the signals of these various stereoisomers resonate at similar frequency, and, thus, there are overlapping peaks. See Geraldes, C. F., et al., *Inorganic Chemistry*, 32: 2426-2432 (1993); Lammers, H., et al., *Inorganica Chimica Acta*, 268: 249-255 (1998); Lammers, H., et al., *Inorganic Chemistry*, 36: 2527-2538 (1997); Aime, S., et al., *Journal of American Chemical Society*, 121: 5762-5771 (1999); and Choppin, G. R., et al., *Inorganic Chemistry*, 18: 1330-1332 (1979), which are hereby incorporated by reference in their entirety. The broadening that occurs in the NMR spectra is due the conformational mobility of the ligand around the metal. See Peters, J. P., et al., *Inorganic Chemistry*, 27 (1988), which is hereby incorporated by reference in its entirety. The coordination geometry of the complex is fluxional. As the temperature increases, the NMR peaks coalesce to exhibit nine distinct peaks for the acetates and methylene groups. See Aime, S., et al., *Journal of American Chemical Society*, 121: 5762-5771 (1999), which is hereby incorporated by reference in its entirety. Lee has looked at La complexes of triethylentetraaminehexacetic acid (TTHA) via NOSEY experiment and has stated that the recoordination is occurring through a bond-breaking mechanism and this accounts for the different peaks observed in the spectra. See Lee, S., et al. *Magnetic Resonance in Chemistry*, 38: 820-822 (2000), which is hereby incorporated by reference in its entirety. Peters has also examined the LnDTPA-bisamide complexes and notice the same occurrences. See Geraldes, C. F., et al., *Inorganic Chemistry*, 32: 2426-2432 (1993) and Lammers, H., et al., *Inorganica Chimica Acta*, 268: 249-255 (1998), which are hereby incorporated by reference in their entirety. This seems to be occurring for the LaDTPA-bis amide complex, 4. The $^1$H NMR spectra of both 4 and functionalized silver particles, 8, have various peaks which are not fully resolved. See FIGS. 10A-C. The next step is to examine the $^{13}$C NMR of ligand, 4, and functionalized silver particles, 8.

Figure 12A:
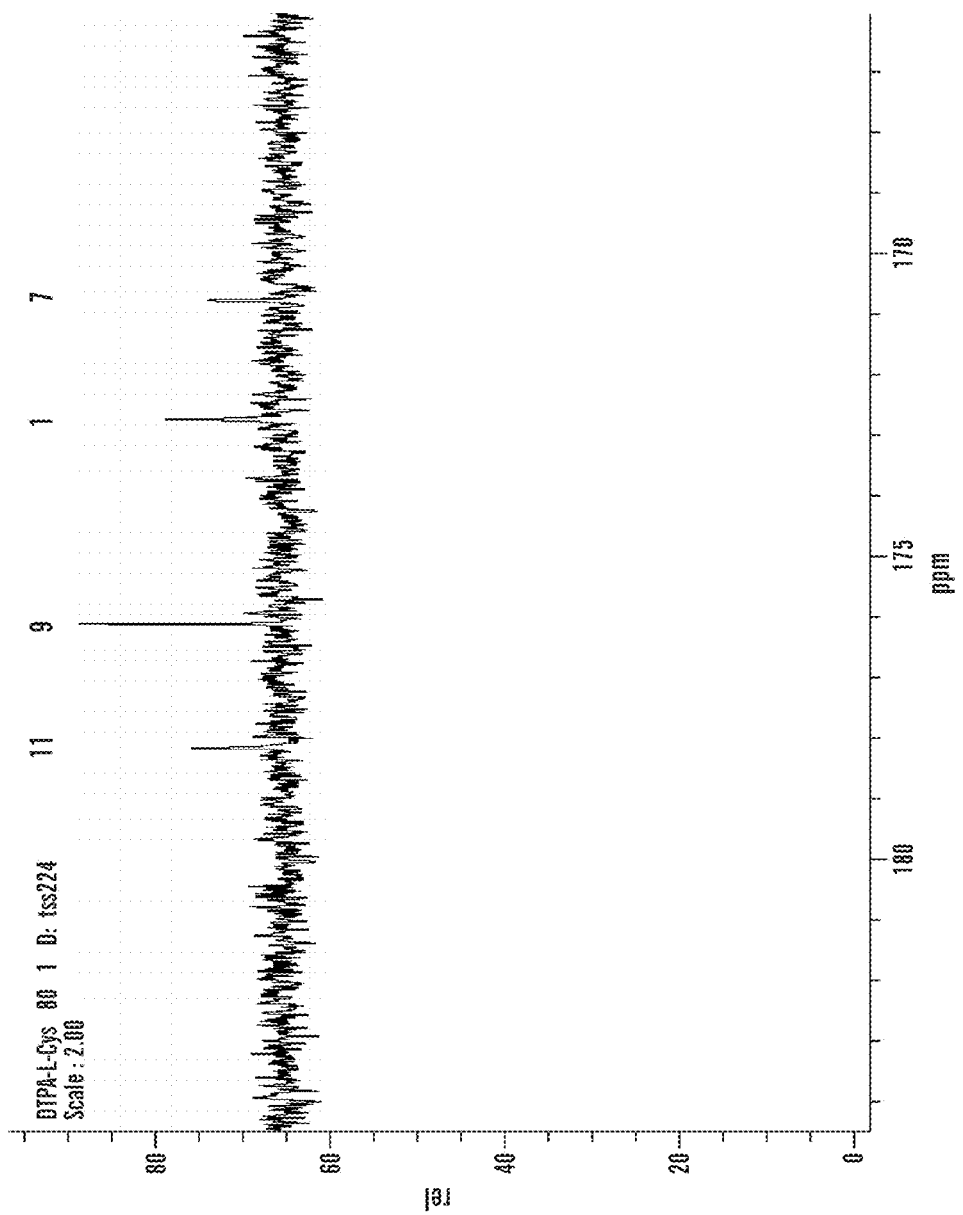
FIGS. 12A-C show $^{13}$C NMR spectra for comparison of the carbonyl regions for Compound 2 (FIG. 12A), Construct 6 (FIG. 12B), and Compound 8 (FIG. 12C), in $D_2O$.
Figure 12B:
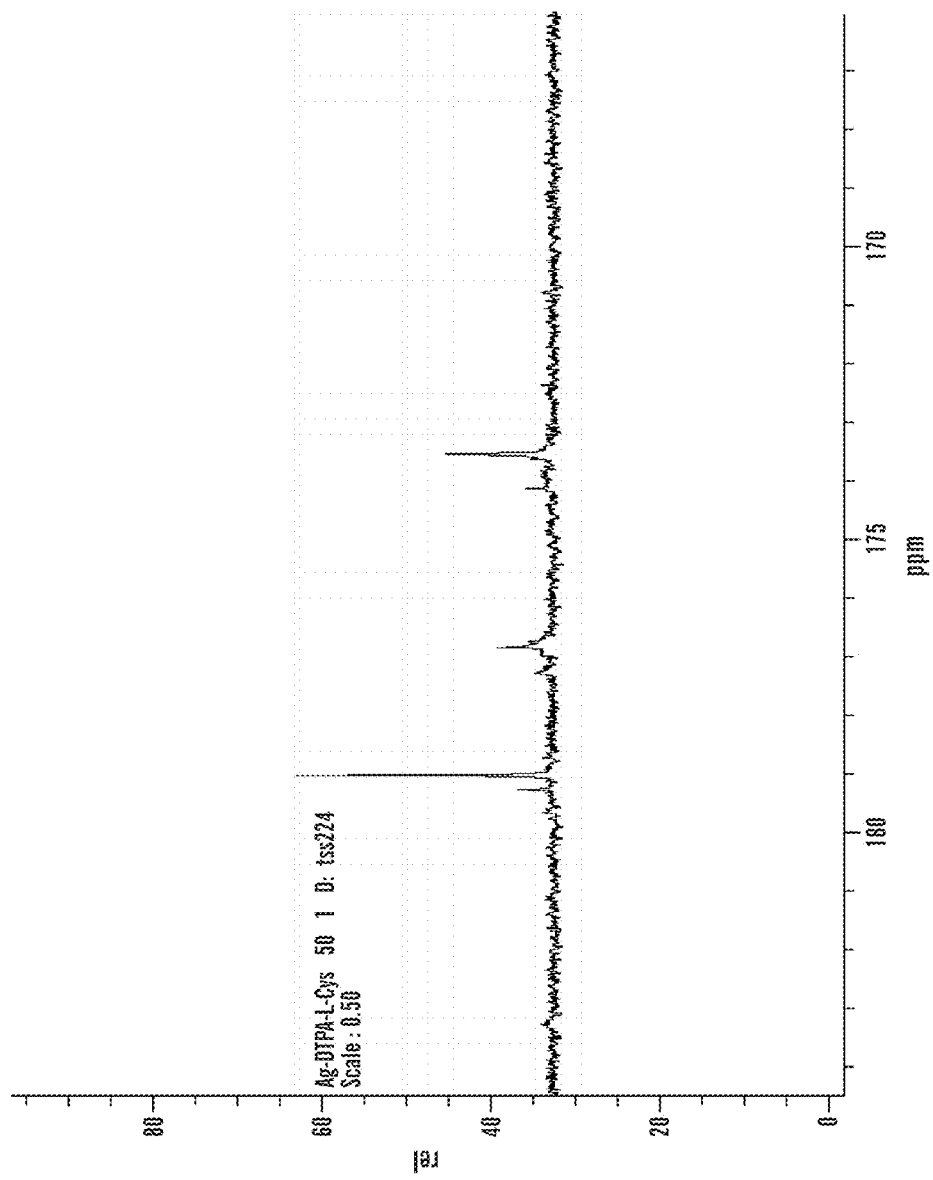
Figure 12C:
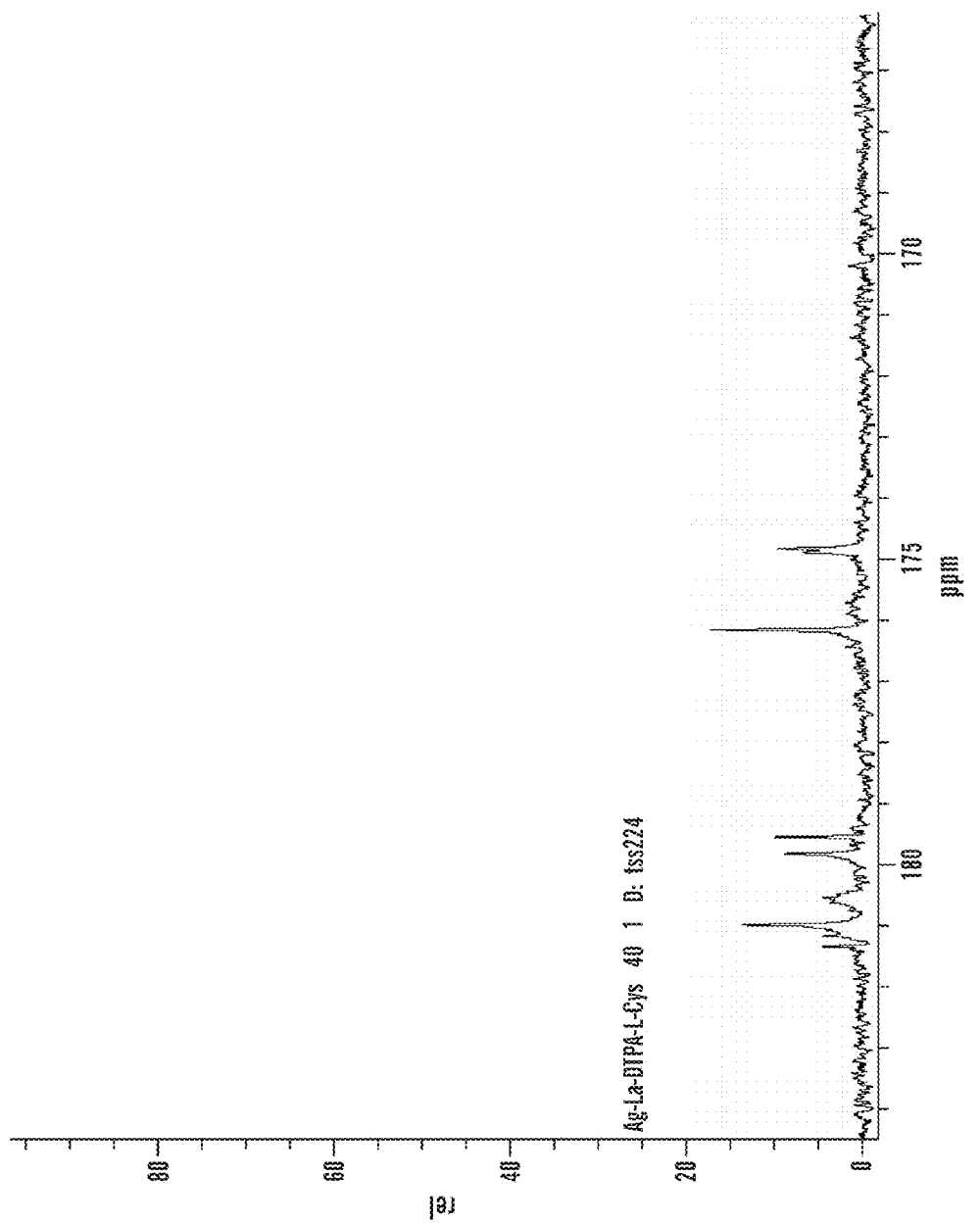

The $^{13}$C NMR shows multiple broadened carbonyl peaks as seen in FIGS. 12A-C. This was observed by Peters and Aime with their DTPA complexes and this shows the presence of multiple stereoisomers. See Aime, S., et al., *Journal of American Chemical Society*, 121: 5762-5771 (1999); Geraldes, C. F., et al., *Inorganic Chemistry*, 32: 2426-2432 (1993); Lammers, H., et al., *Inorganica Chimica Acta*, 268: 249-255 (1998); Lammers, H., et al., *Inorganic Chemistry*, 36: 2527-2538 (1997); and Peters, J. P., et al., *Inorganic Chemistry*, 27 (1988), which are hereby incorporated by reference in their entirety.

Figure 13A:
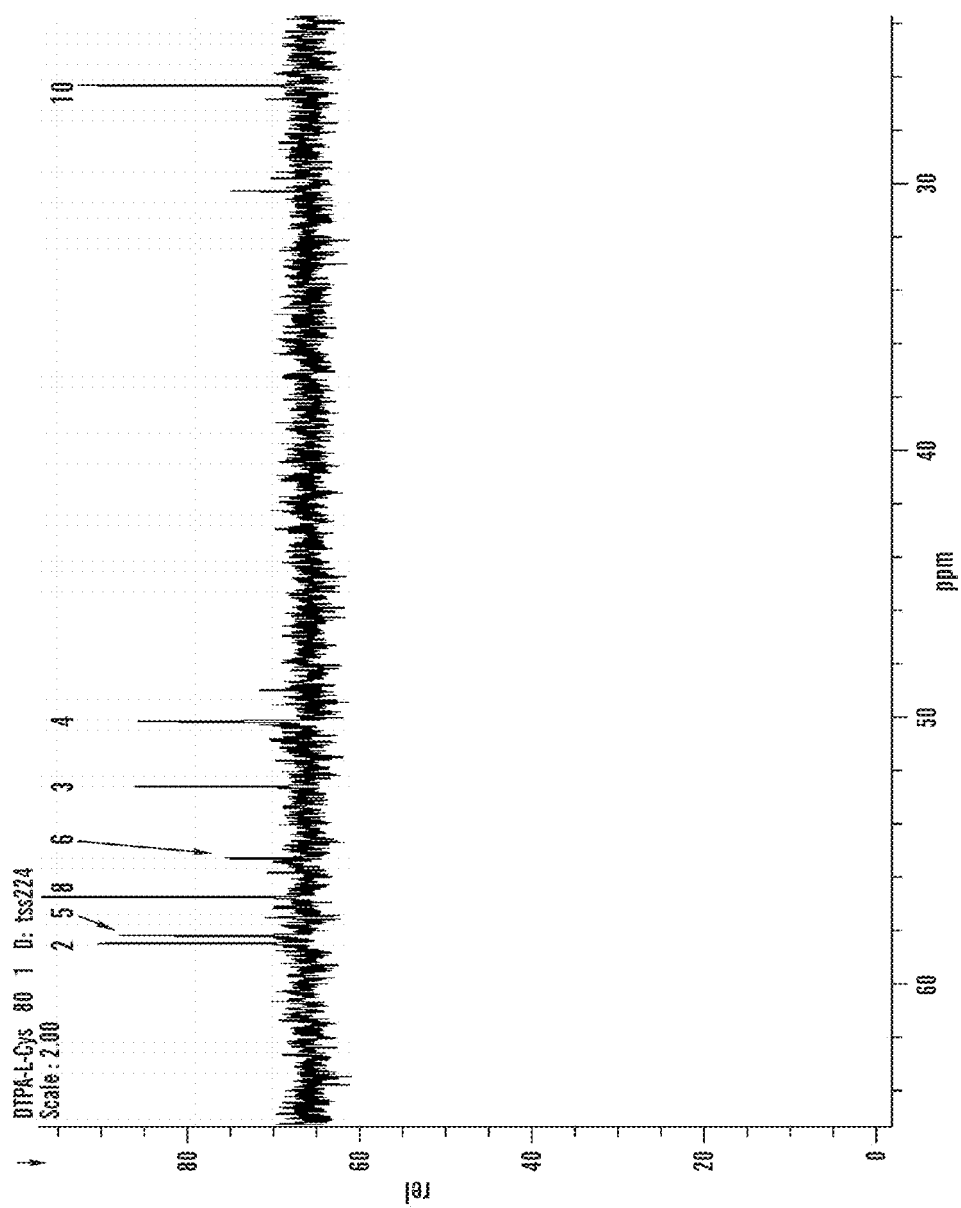
FIGS. 13A-C show $^{13}$C NMR spectra for comparison of the aliphatic regions for Compound 2 (FIG. 13A), Construct 6 (FIG. 13B), and Compound 8 (FIG. 13C), in $D_2O$.
Figure 13B:
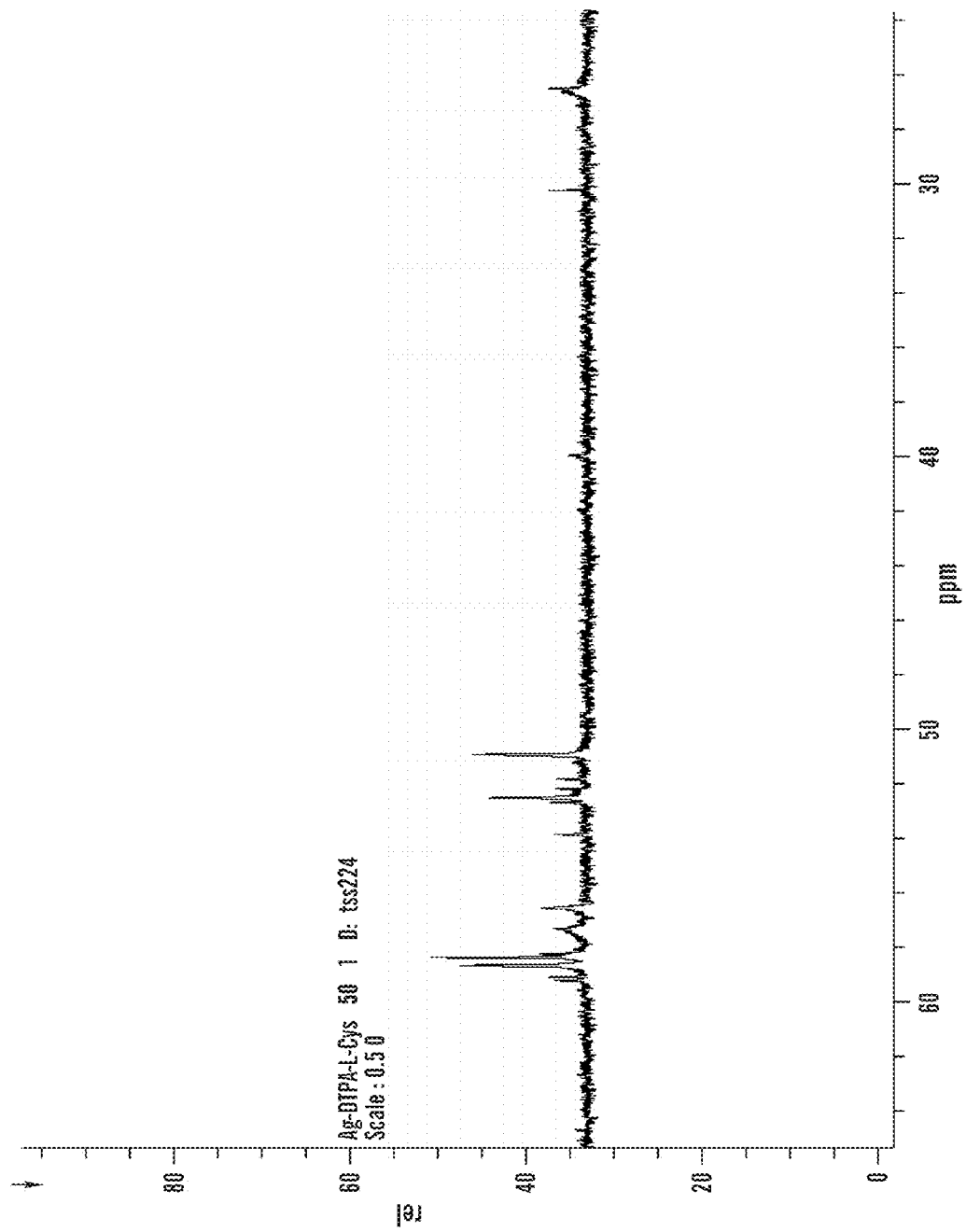
Figure 13C:
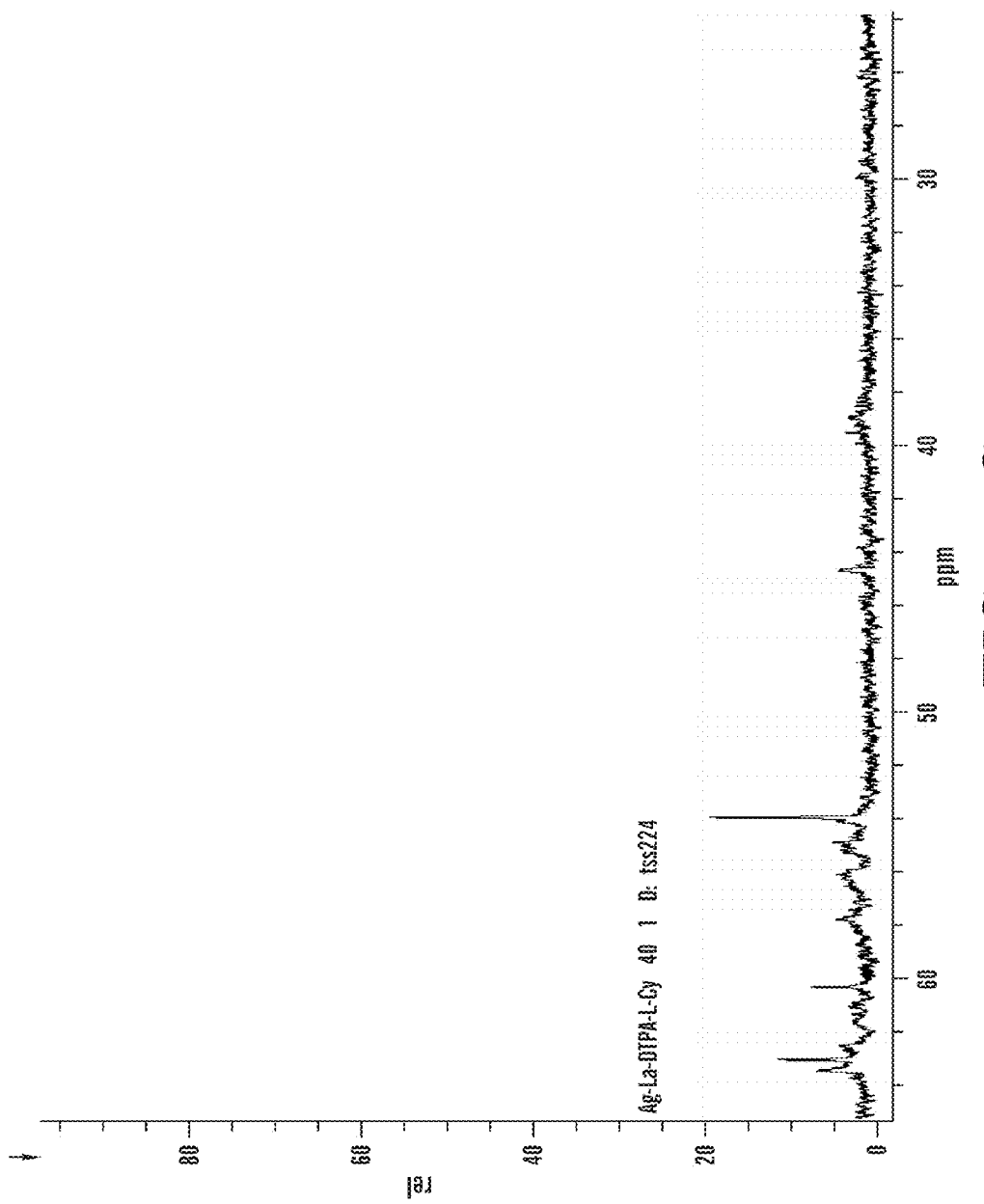

When examining the aliphatic region, there are a few sharp peaks, but, in general, broadened peaks are seen in FIG. 13C, which were also observed by Peters and Aime at room temperature for their ligands. See Aime, S., et al., *Inorganica Chimica Acta*, 177: 101-105 (1990); Geraldes, C. F., et al., *Inorganic Chemistry*, 32: 2426-2432 (1993); and Lammers, H., et al., *Inorganica Chimica Acta*, 268: 249-255 (1998), which are hereby incorporated by reference in their entirety. Also in the same spectra, there is a new broad peak at 38 ppm which according to Rajarathnam is due to the βC on the cysteine that has been oxidized. See Sharma, D., et al., *Journal of Biomolecular NMR*, 18: 165-171 (2000), which is hereby incorporated by reference in its entirety. This shows that some of the ligand has oxidized to the disulfide. This peak is seen to a very small degree in spectra B (see FIG. 13B) for Construct 6, but is a relatively small peak which shows only some ligand has been oxidized. The one positive feature in spectra C (see FIG. 13B) is the peak at 25 ppm has been broadened into the baseline. The absence of this peak shows that the thiols have bound to the surface of the silver. See Terrill, R. H., et al., *Journal of American Chemical Society*, 117: 12537-12548 (1995), which is hereby incorporated by reference in its entirety.

Figure 14:
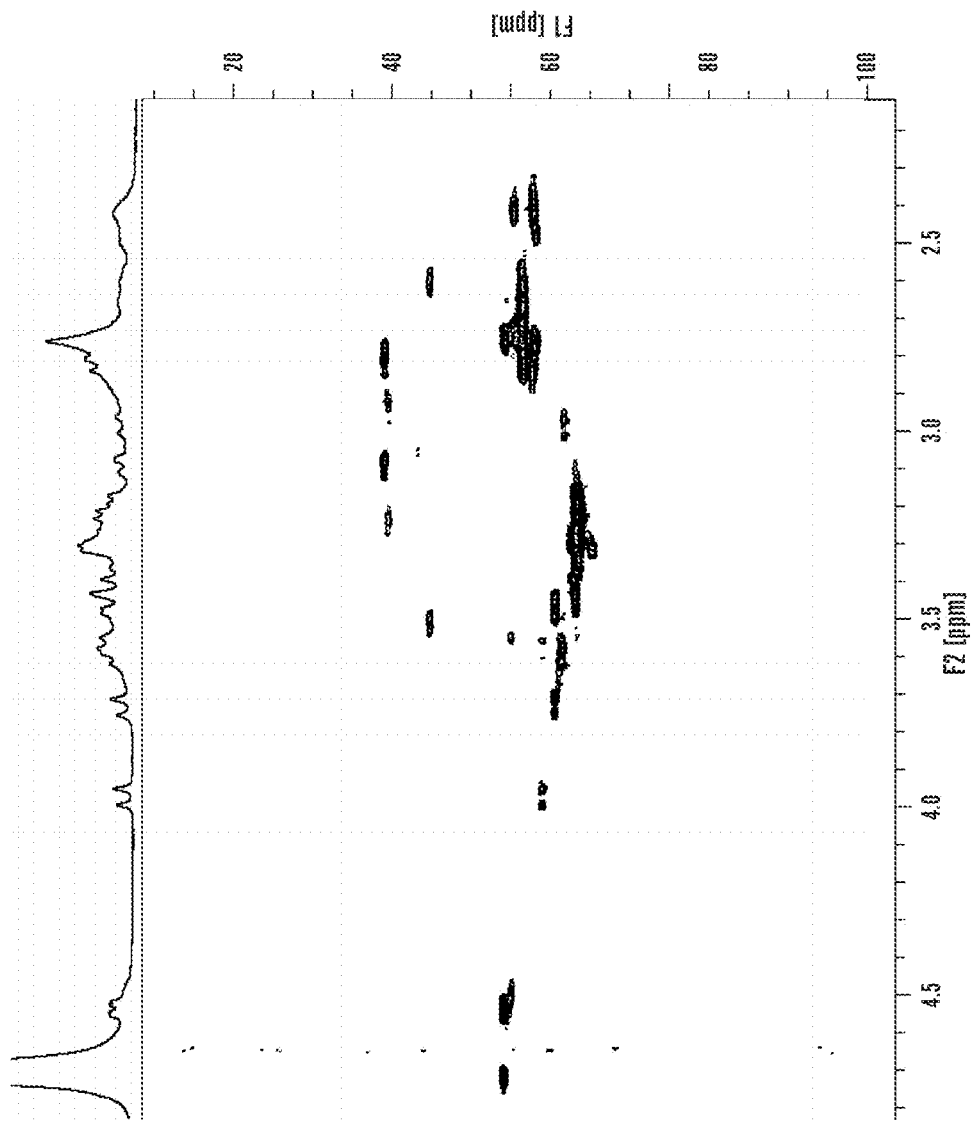
FIG. 14 shows a Heteronuclear Single Quantum Correlation (HSQC) spectrum of Compound 8 in $D_2O$.

The HSQC spectrum was also examined to fully characterize compound 8. See FIG. 14.

Example 13

CNTA Synthesis and Characterization

The synthesis of 5 was based on a modification of an earlier preparation of the same molecule by Michaelis and Schubert. See Michaelis, L., et al., *Journal of Biological Chemistry*, 106: 1 (1934), which is hereby incorporated by reference in its entirety. $K_3CNTA.4H_2O$, as the isolated form of the product, as indicated by elemental analysis differs from the expected stoichiometry of $K_4CNTA$. The isolated form is likely consistent with a mixture of $K_3CNTA$ and $K_4CNTA$.

In order to demonstrate the bonding of the ligand to the silver nanoparticles, $^1H$ NMR data was acquired. See Terrill, R. H., et al., *Journal of American Chemical Society*, 117: 12537-12548 (1995), which is hereby incorporated by reference in its entirety. The spectrum of 9 shows significant broadening of all peaks compared to those of the free ligand (see FIG. 14). The degree of broadening is expected to decrease with the distance of the proton from the silver surface. The peaks were assigned on the basis of the splitting pattern. The peak present at 3.31 ppm is due to residual methanol.

Figure 15A:
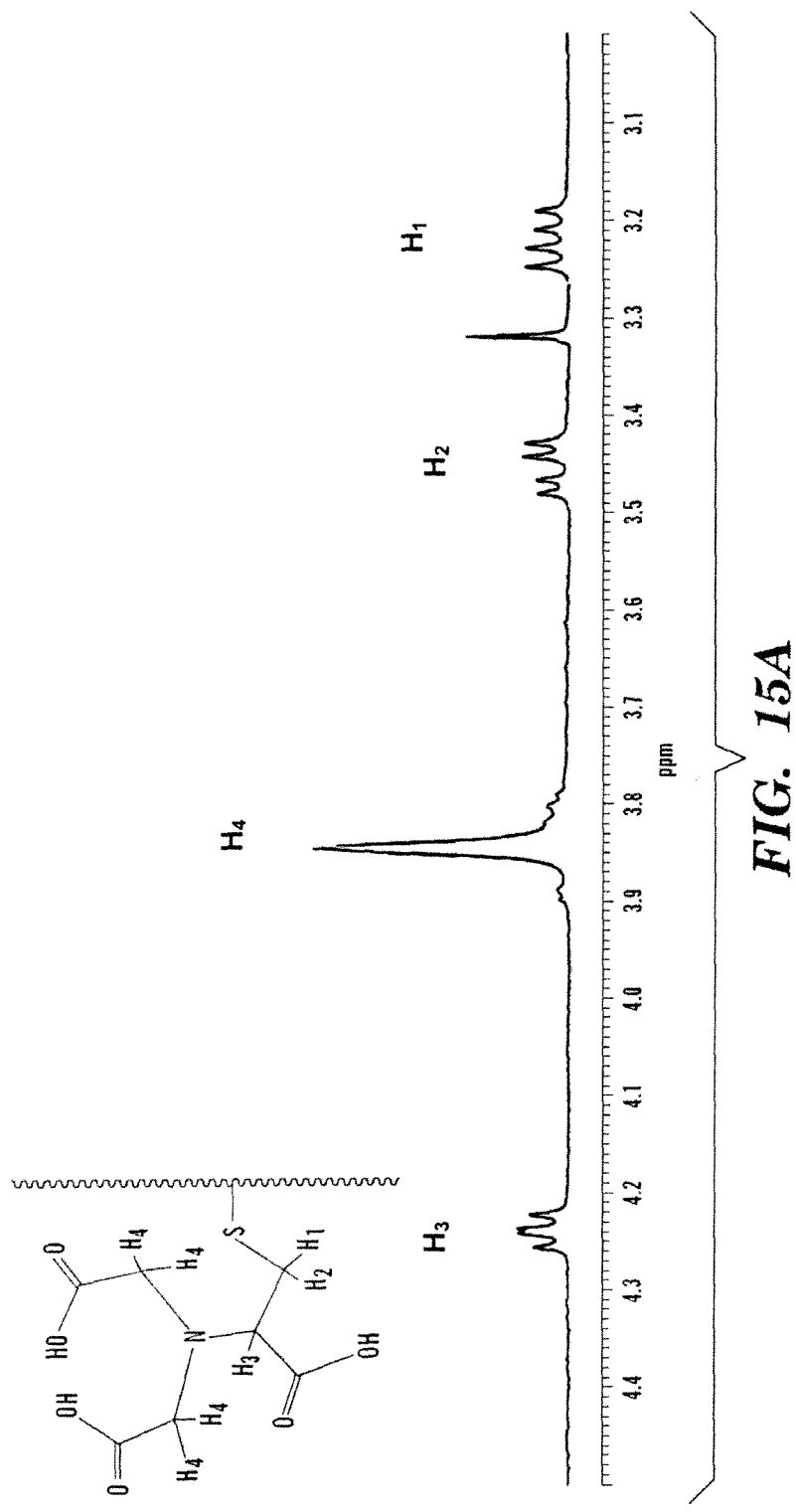
FIGS. 15A-B show $^1$H NMR spectra of Compound 5 (FIG. 15A) and Compound 9 (FIG. 15B), in $D_2O$.
Figure 15B:
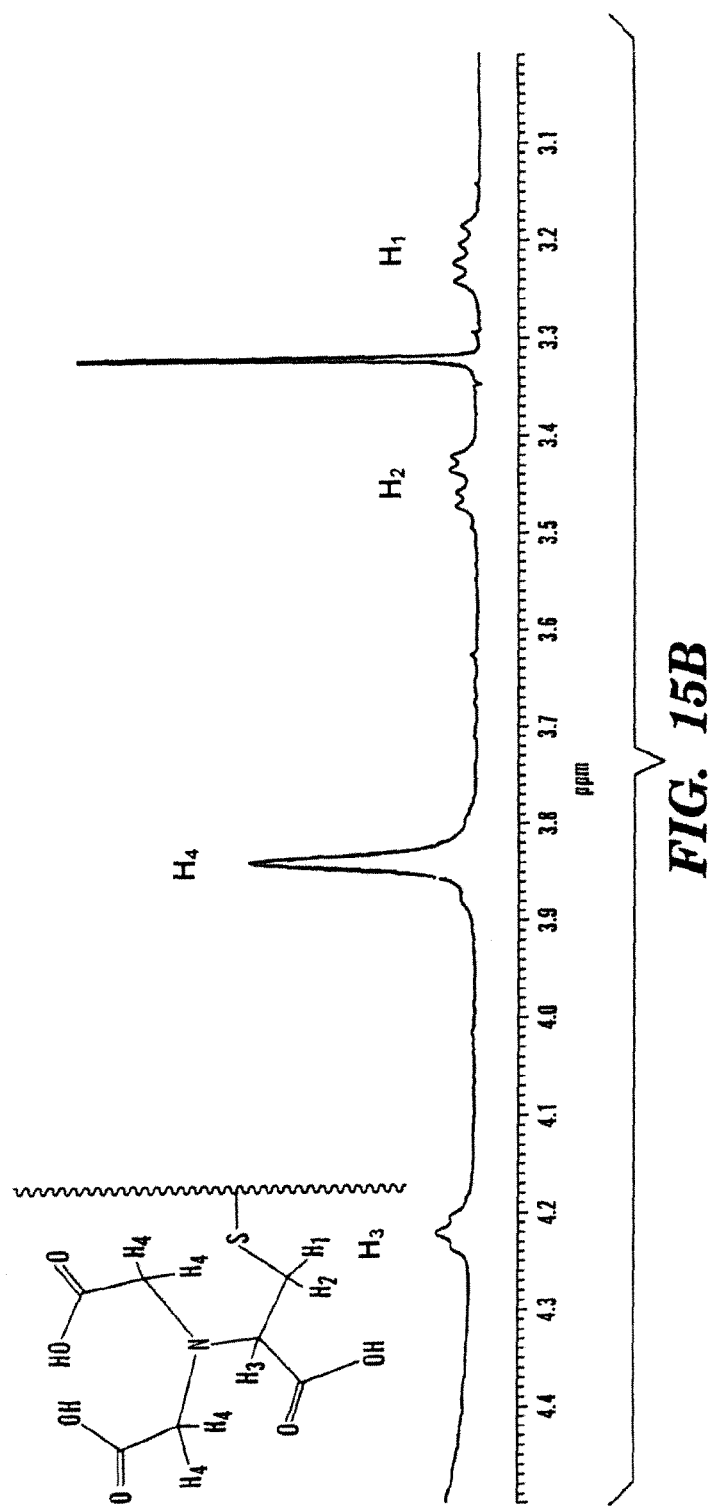
Figure 16A:
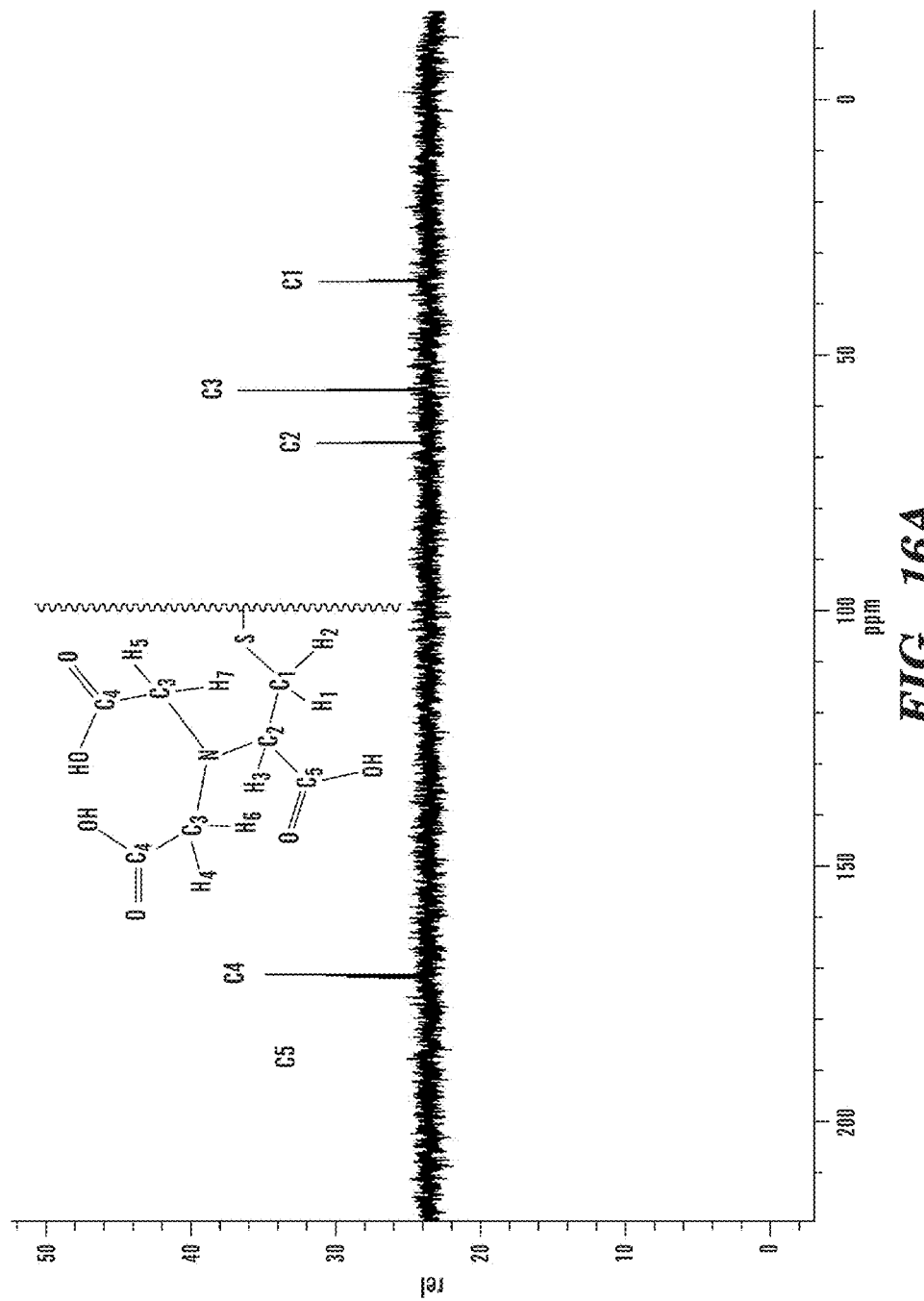
FIGS. 16A-B show $^{13}$C NMR spectra of Compound 5 (FIG. 16A) and Compound 9 (FIG. 16B), in $D_2O$.
Figure 16B:
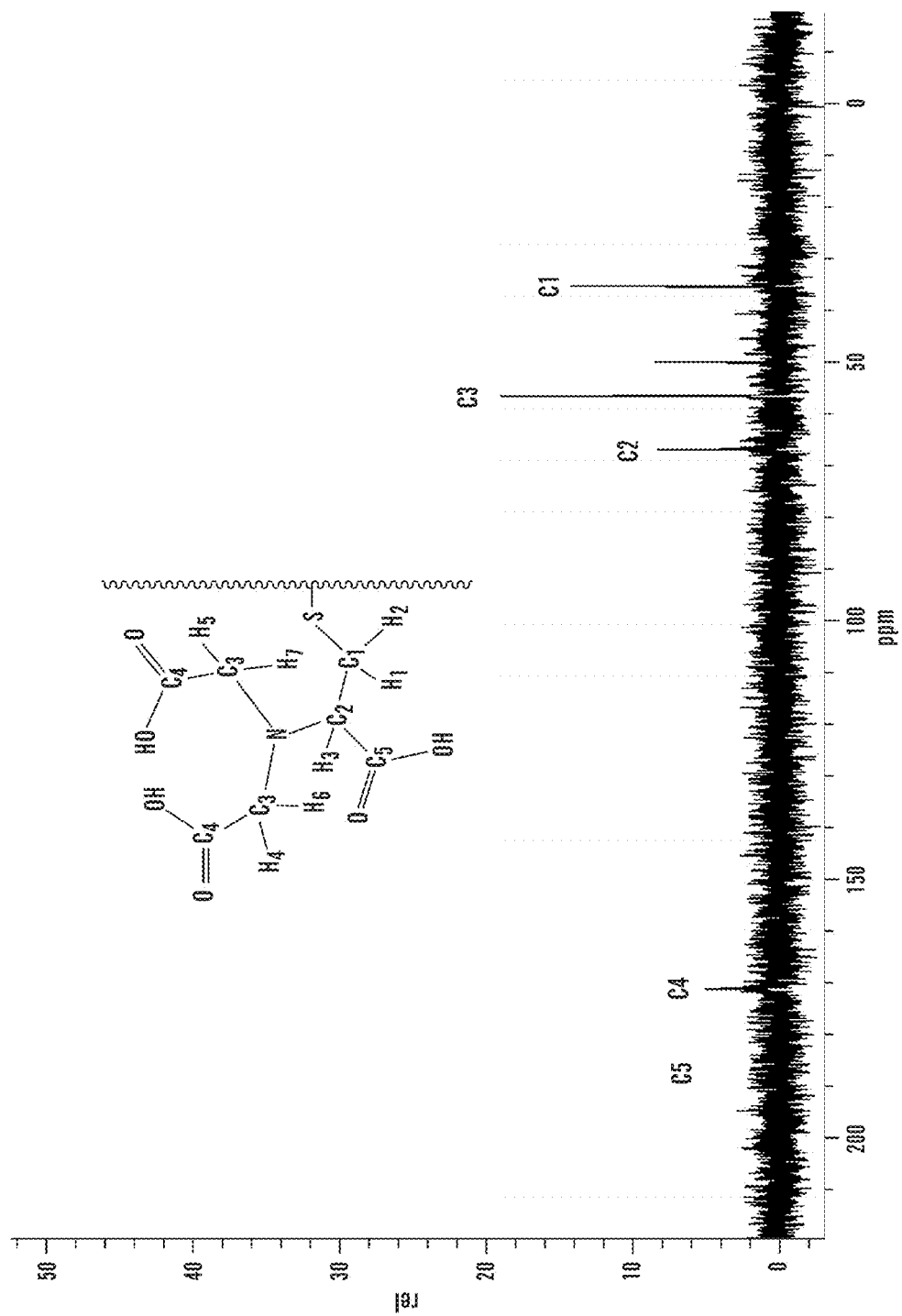

$^{13}C$ NMR data revealed a diminution of the carbonyl peaks for 9, which suggests that carboxylate groups also bind to the silver surface. See FIGS. 15A-B. It is also noteworthy that the signal for the carbon closest to the silver surface was still detectable after binding the molecule to the silver surface.

Figure 17:
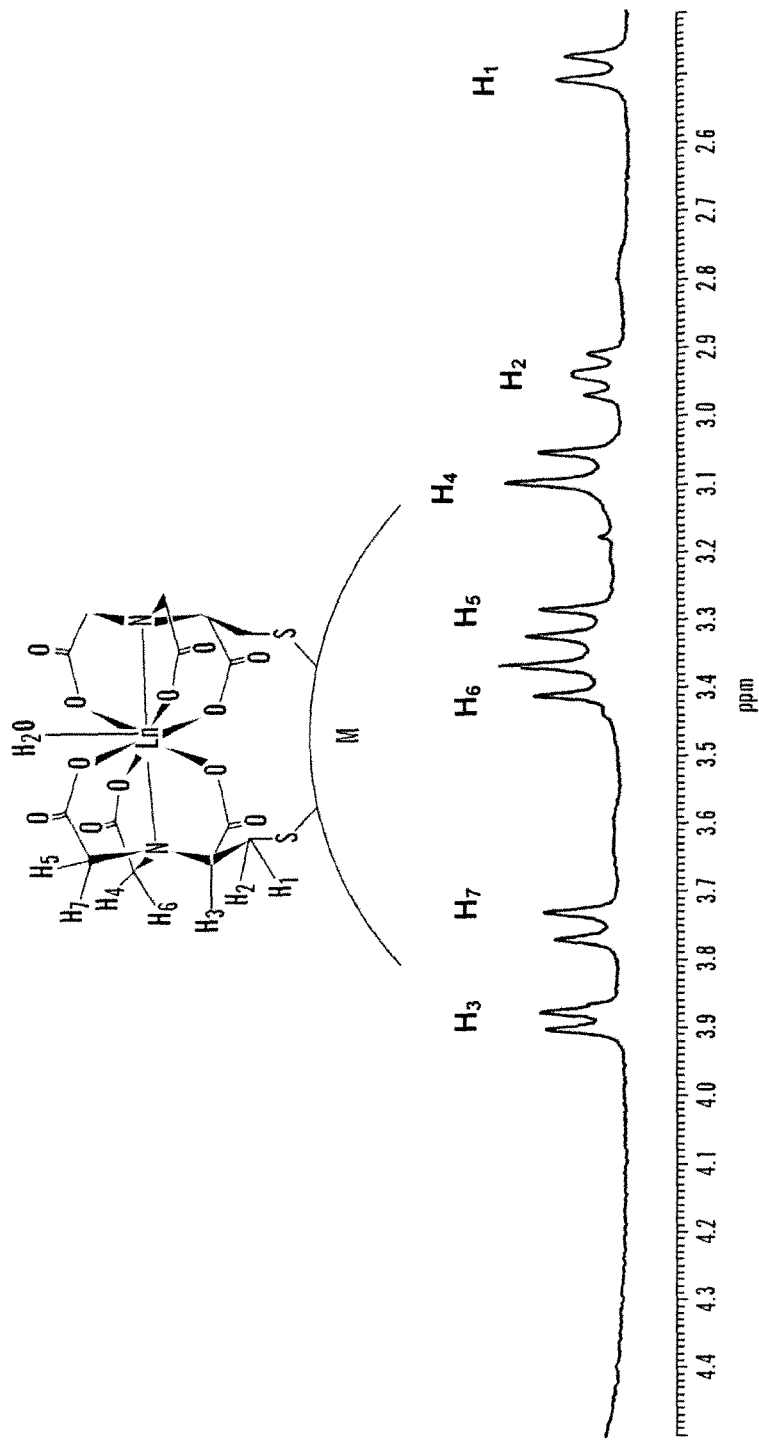
FIG. 17 shows a $^1$H NMR spectrum of Compound 10.
Figure 18A:
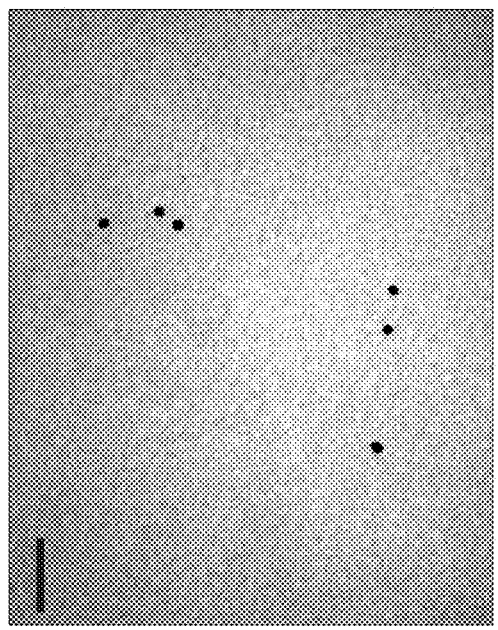
FIGS. 18A-D show Transmission Electron Microscopy (TEM) images of gold particles (FIG. 18A), silver particles (FIG. 18B), Construct 6 (FIG. 18C), and Compound 8 (FIG. 18D).
Figure 18B:
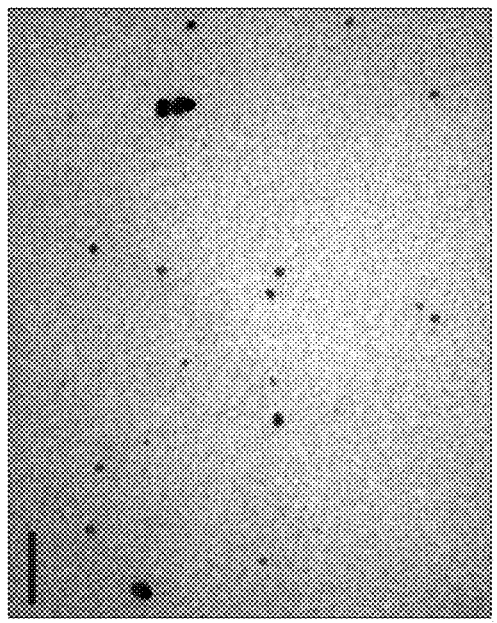
Figure 18C:
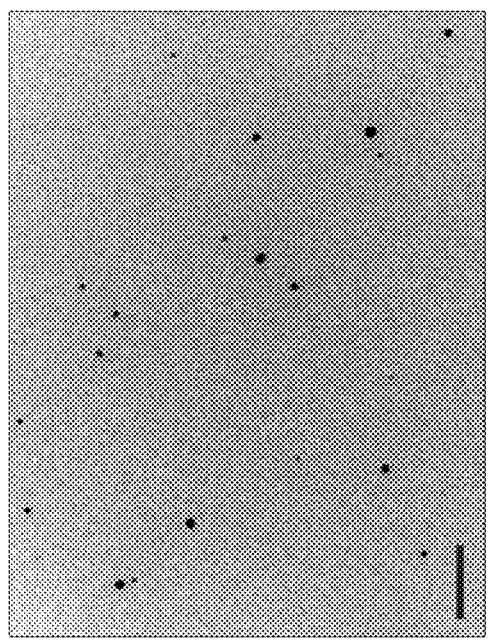
Figure 18D:
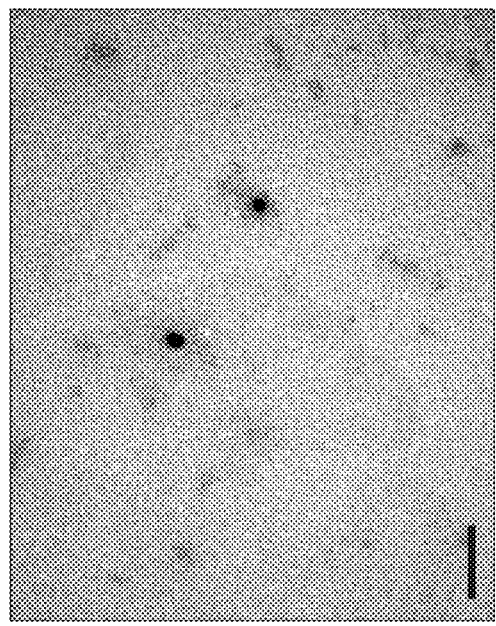
Figure 19A:
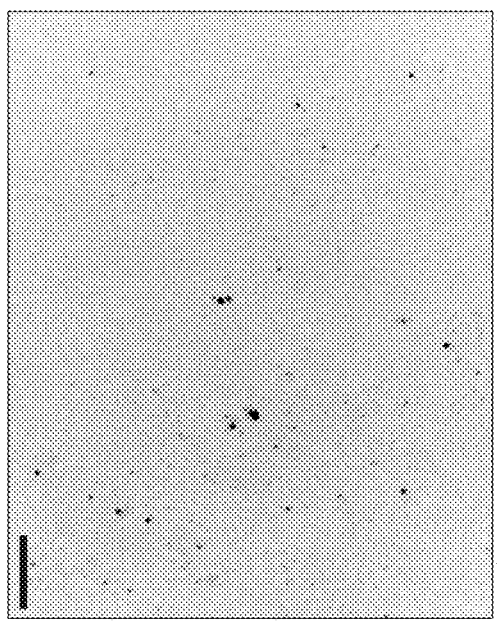
FIGS. 19A-D show Transmission Electron Microscopy (TEM) images of Compound 9 (FIGS. 19A-B) and Compound 11 (FIGS. 19C-D).
Figure 19B:
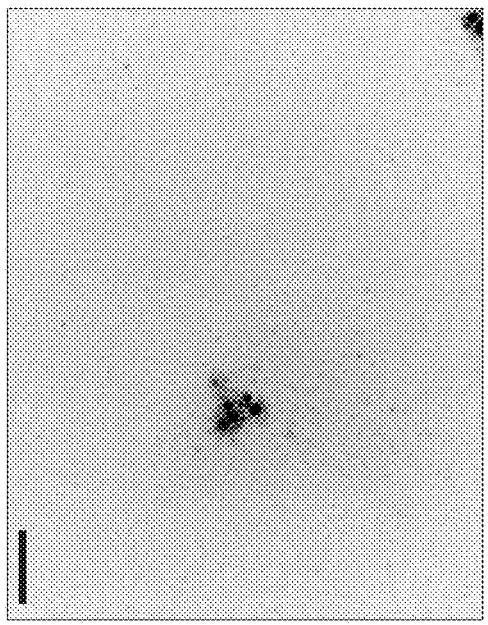
Figure 19C:
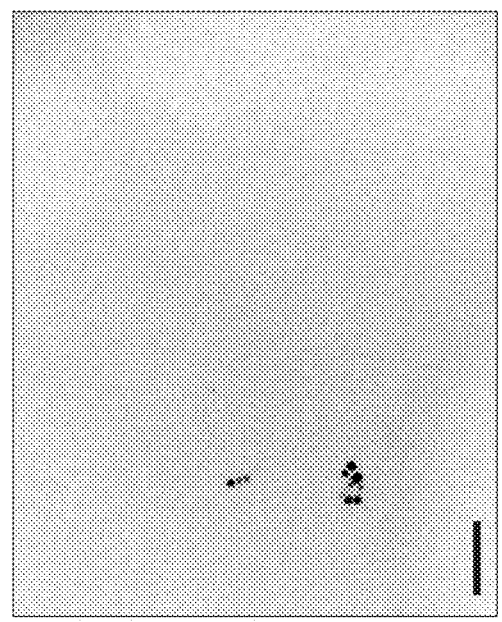
Figure 19D:
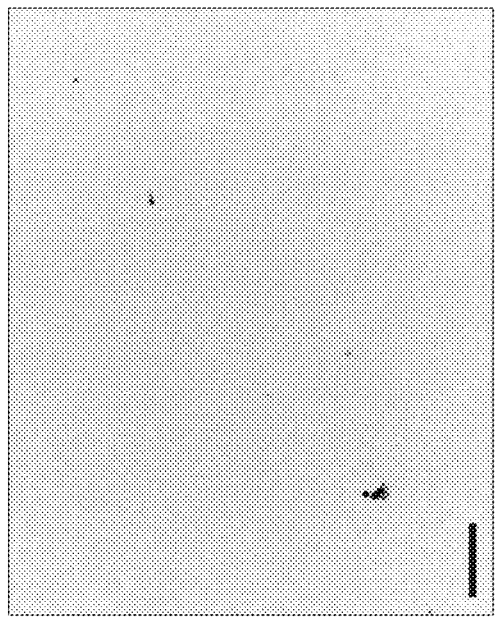

$^1H$ NMR data of 10 (see FIG. 17) gave rise to a number of peaks previously unobserved in 9. It is believed that this is a result of asymmetry of the H4 hydrogens (as labeled in FIG. 15) arising upon complexation. The framework for this interpretation comes from a report on the complex lanthanum(III) triethylenetetraaminehexaacetic acid, as previously reported by Lee. See Lee, S., et al. *Magnetic Resonance in Chemistry*, 38: 820-822 (2000), which is hereby incorporated by reference in its entirety. In this study, a subset of the proton resonances observed in the free ligand doubled upon lanthanum complexation.

Example 14

UV-Visible Spectra

Bare silver nanoparticles have been reported to have UV-Vis absorption spectra with a peak at 392 nm. See Joo, T. H., et al., *Chemical Physics Letters*, 112 (1): 65-68 (1984), which is hereby incorporated by reference in its entirety. The silver particles were prepared according to this published method and gave an absorption spectra with a peak at 389 nm. See Table 1. See Joo, T. H., et al., *Chemical Physics Letters*, 112 (1): 65-68 (1984), which is hereby incorporated by reference in its entirety. A red shift occurred in the absorption spectra when the DTPA derivative 2 and the GdDTPA derivative 3 were bound to the surface of the particles. Construct 6 and Compound 7 produced a red shift in the absorption spectra to the wavelengths of 395 and 408 nm, respectively. In a second set of constructs consisting of CNTA on silver 9, and GdNTA on silver 11, the same red shift occurred which resulted in a shift of the absorption peaks from 406 and 414 nm, respectively. With the second set of ligands, compounds 9 and 11, the same red shift occurred, shifting the peaks to 406 nm and 414 nm, respectively. As more of the surface of the silver particle gets functionalized by the ligand, there is a red shift in the absorption spectra, as reported by Kim with respect to their amino acids on silver. See Joo, T. H., et al., *Chemical Physics Letters*, 112 (1): 65-68 (1984) and Aryal, S., et al., *Journal of Colloid and Interface Science*, 299: 191-197 (2006), which are hereby incorporated by reference in their entirety. By means of the absorption band shift, it can be shown that the silver particles have been functionalized with thiols.

TABLE 1

Table 1. UV-Vis absorbance peaks

| Compound | Absorbance nm |
|---|---|
| Bare Ag Nanoparticles | 389 |
| Construct 6 | 395 |
| Compound 7 | 408 |
| Compound 9 | 406 |
| Compound 11 | 414 |

Example 15

Transmission Electron Microscopy (TEM)

TEM images were obtained for Construct 6 and Compound 7. See FIGS. 18A-D. Particle aggregation occurred to varying extents for both samples, which may be attributed to the charge of the overall particle.

TEM images were obtained for Compound 9 and Compound 11. See FIGS. 19A-D. Particle aggregation occurred to varying extents for both samples.

Example 16

Determination of Ligands per Particle

Surface coverage of the functionalized silver nanoparticles by the various ligands was determined by examining the thermogravimetric analysis (TGA) profiles of these constructs. The number of ligands and ligand-gadolinium complexes present in the samples and the mass due to these was determined by the mass percent of organic material present, as indicated by the TGA profiles. By then assuming that the remaining inorganic mass was silver, the number of silver particles present was determined by the density of bulk silver (10 g/cm$^3$) and the size of the particles (10 nm) using TEM. The ratio of ligands per particle was then calculated.

The average of the ligand population on the silver core in the nanoparticle construct was determined by examining the TGA profiles. For any given mass of a nanoparticle construct, the ligand population can be determined by comparing the percent organic to the total mass of the particle.

The mass of the silver core for a given mass of nanoparticle construct was determined by using the average radius and density of particles. The average radius of silver nanoparticles, as determined by TEM images, is 10 nm and the density is 7.56 g/cm$^3$. It is known that the ratio of gadolinium to ligand is 1:1. This binding relationship allows calculation of the concentration of $Gd^{+3}$ for any mass of nanoparticle construct. The number of ligands per particle, as determined for the nanoparticle constructs, is presented in Table 2. These numbers concur with the results reported by Murray et al., on the number of dodecanethiol molecules on a gold nanoparticles. See Terrill, R. H., et al., *Journal of American Chemical*

Society, 117: 12537-12548 (1995), which is hereby incorporated by reference in its entirety.

TABLE 2

Table 2. Ligands per Silver Particle

| Compound | Ligands per Particle |
|---|---|
| Construct 6 | $1.91 \times 10^4$ |
| Compound 7 | $1.78 \times 10^4$ |
| Compound 9 | $1.59 \times 10^4$ |
| Compound 11 | $1.37 \times 10^4$ |

Example 17

$R_1$ Relativity Studies $T_1$ relativity values were determined from a standard inversion recovery pulse sequence of 180°-τ[variable delay]-90°-acquire, and by fitting the equation: $y=A*\{1-[2-\exp(-TR/T1)]*\exp(-\tau/T1)\}$.

Where T1=Longitudinal relaxation time or spin-lattice, A=peak integral at time τ>>T1, TR=total time between scans including the 180-t-90 sequence plus relaxation delay time, τ=delay time t in the 180-t-90 pulse sequence. See Levy et al., *J. Magn. Reson.*, 11: 58 (1973), which is hereby incorporated by reference in its entirety.

Relaxivity values were determined by calculating the slope of a graph of $r_1$ ($1/T_1$) vs. Gd concentration. For all compounds $R_1$ is per $Gd^{+3}$ ion.

TABLE 3

Table 3. $R_1$ Relaxivity per Gd at 9.4T

| Compound | Relaxivity $mM^{-1}Sec^{-1}$ |
|---|---|
| GdDTPA | 5.232 |
| Compound 3 | 9.1785 |
| Compound 7 | 5.9821 |
| Compound 10 | 5.9395 |

Example 18

Thermogravimetric Analysis (TGA)

The thermogravimetric analysis was preformed on Texas Instruments SDT Q600, and the profiles were acquired by using a Universal Analysis program.

Figure 20:
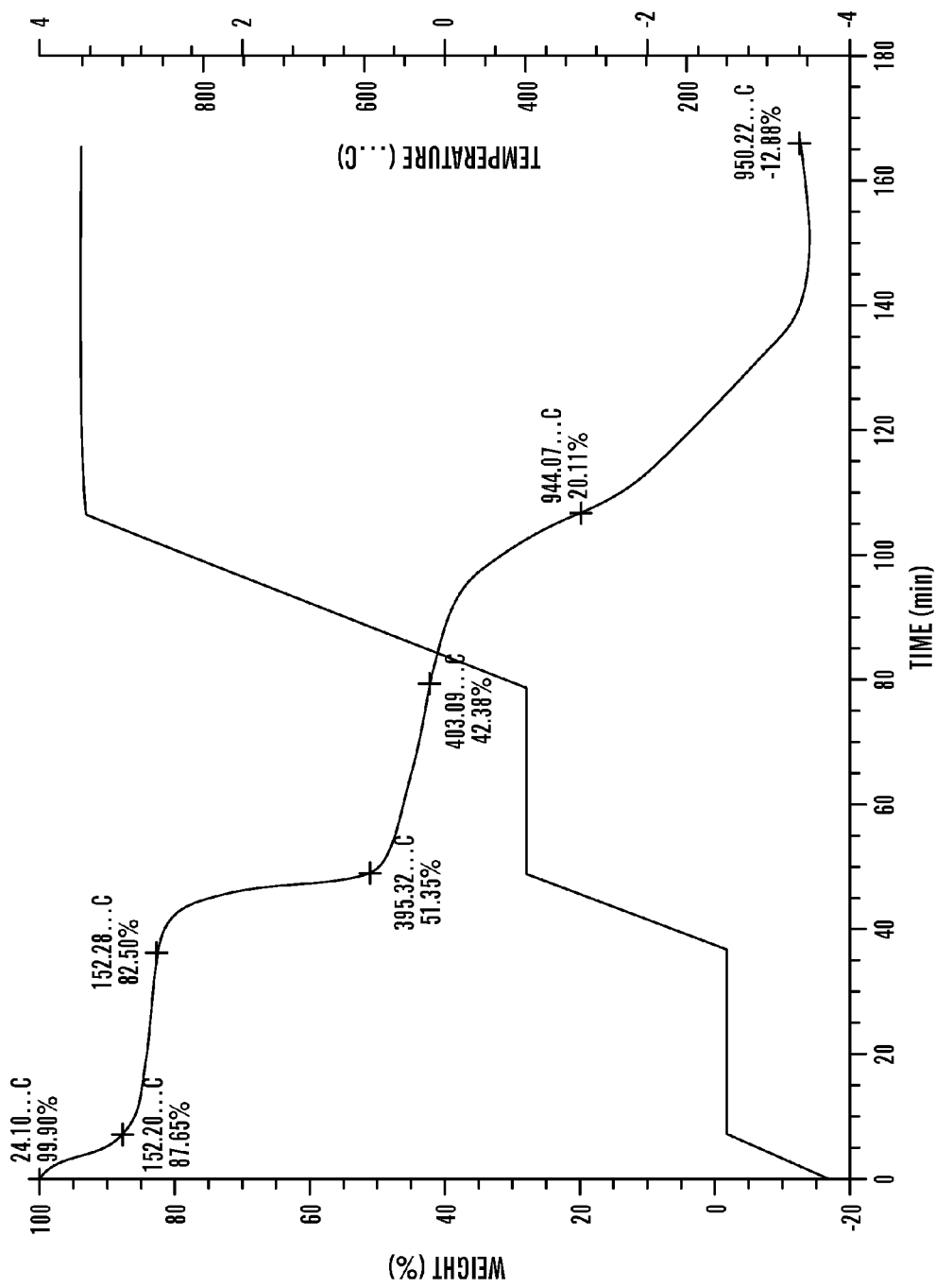
FIG. 20 shows a Thermogravimetric Analysis (TGA) profile of Ag-DTPA-L-Cys.

Ag-DTPA-L-Cys:

In the percent weight loss curve for Ag-DTPA-L-Cys, the first sharp step (30.37%) in the interval 25° C.-150° C. shows the loss of moisture from the compound. The ligand-metal complex is lost in the second step (37.55%) in the temperature interval 150° C.-400° C. The last weight loss step (62.45%) in the interval of 400° C.-950° C. is due to the sublimation of the silver metal particle core. See FIG. 20.

Figure 21:
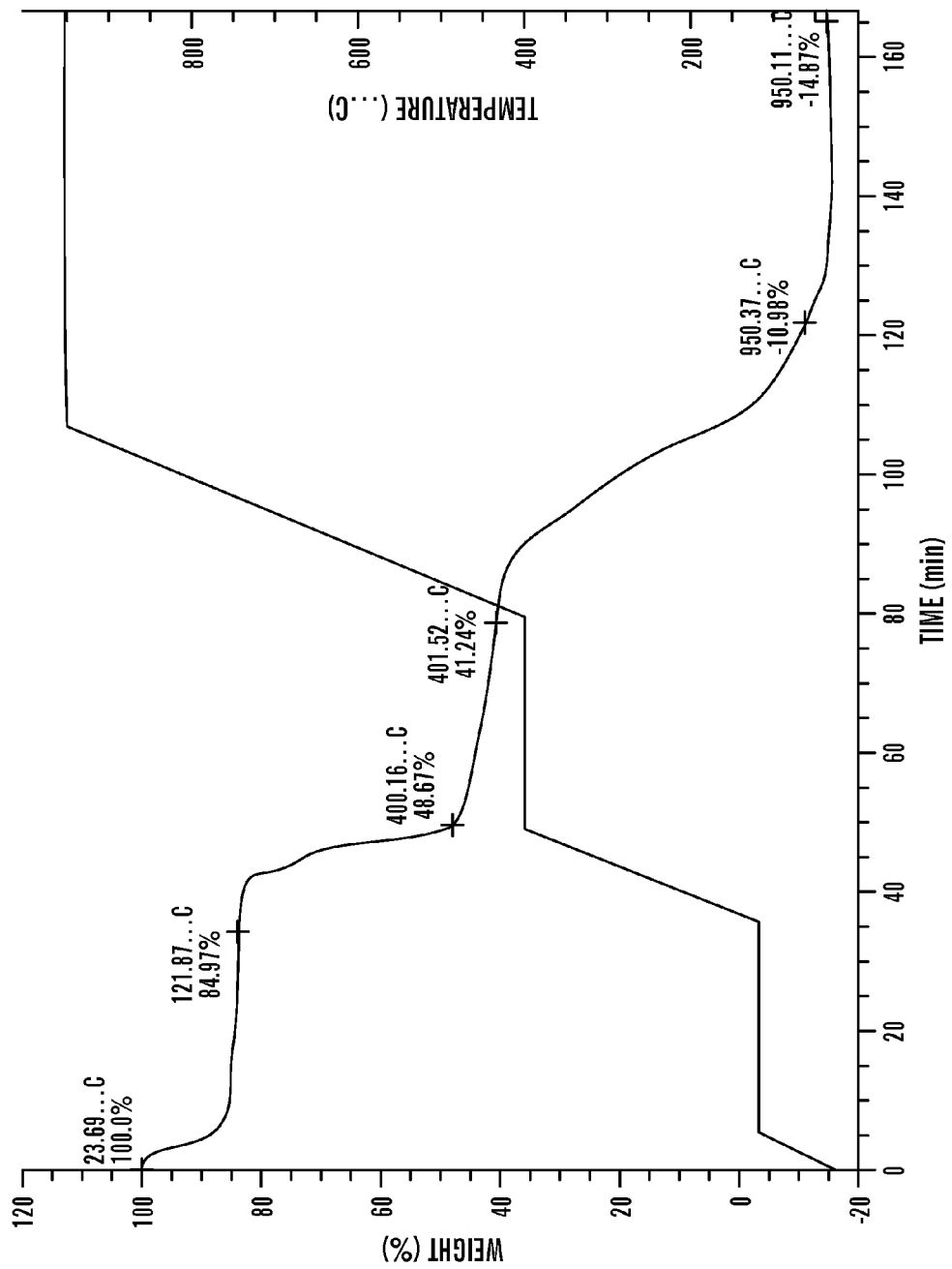
FIG. 21 shows a Thermogravimetric Analysis (TGA) profile of Ag—GdDTPA-L-Cys.

Ag—GdDTPA-L-Cys:

In the percent weight loss curve for Ag-DTPA-L-Cys, the first sharp loss (29.90%) in the interval of 25° C.-150° C. shows the loss of moisture from the compound. The second percent weight loss step (35.90%) in the temperature interval of 150° C.-400° C. is the loss of organic ligand from the surface of the nanoparticle. Last weight loss step (64.10%) in the temperature interval of 400° C.-950° C. is the inorganic silver nanoparticle. See FIG. 21

Figure 22:
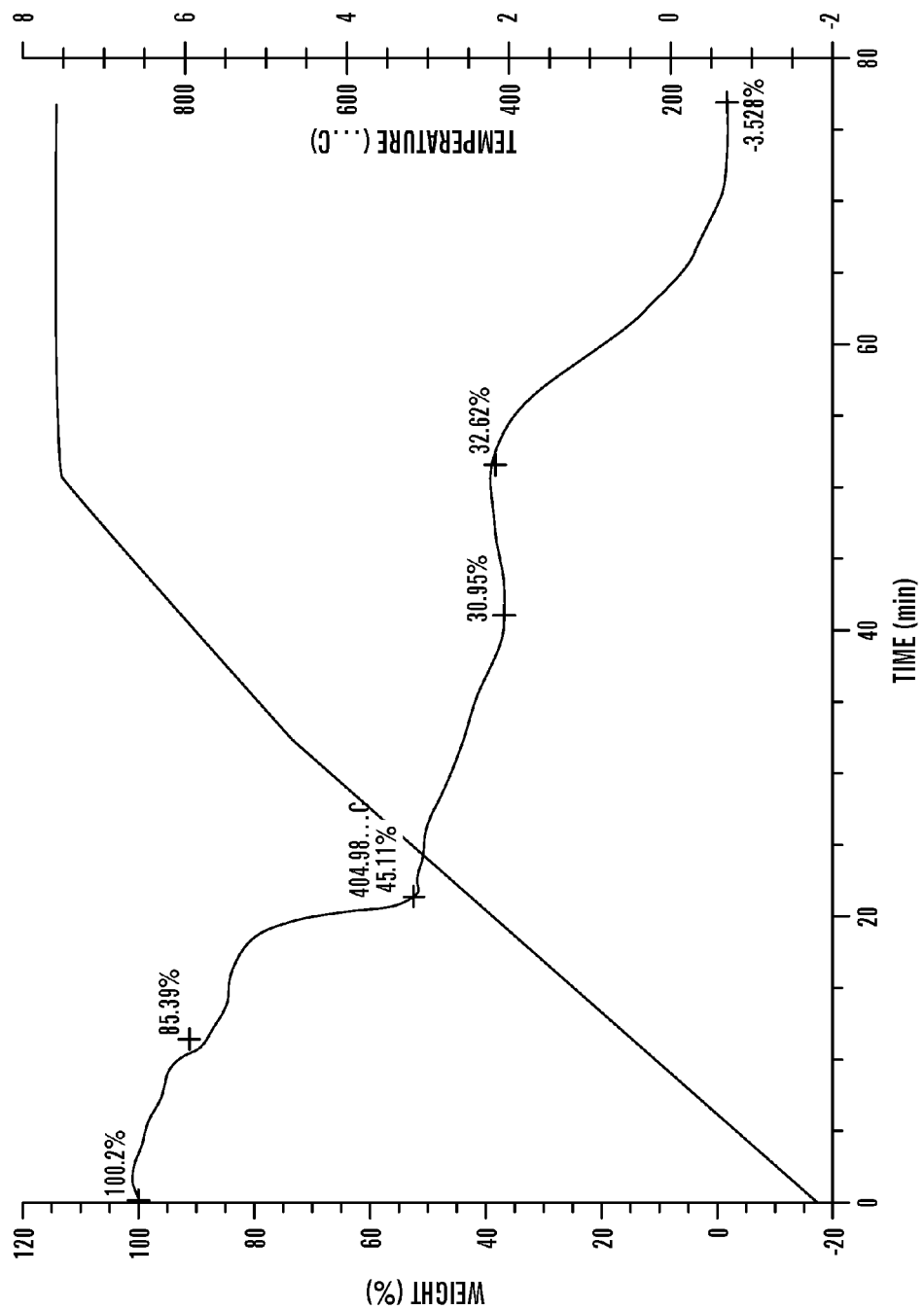
FIG. 22 shows a Thermogravimetric Analysis (TGA) profile of Ag-CNTA.

Ag-CNTA:

In the percent weight loss curve for Ag-CNTA, the first sharp loss (18.34%) during the temperature interval of 25° C.-220° C. shows the loss of moisture from the compound. The second percent weight lost step (31.35%) in the temperature interval of 150° C.-950° C. is the loss of organic ligand from the surface of the nanoparticle. The final weight loss step (68.65%) at the temperature of 950° C. is the inorganic silver nanoparticle. See FIG. 22.

Figure 23:
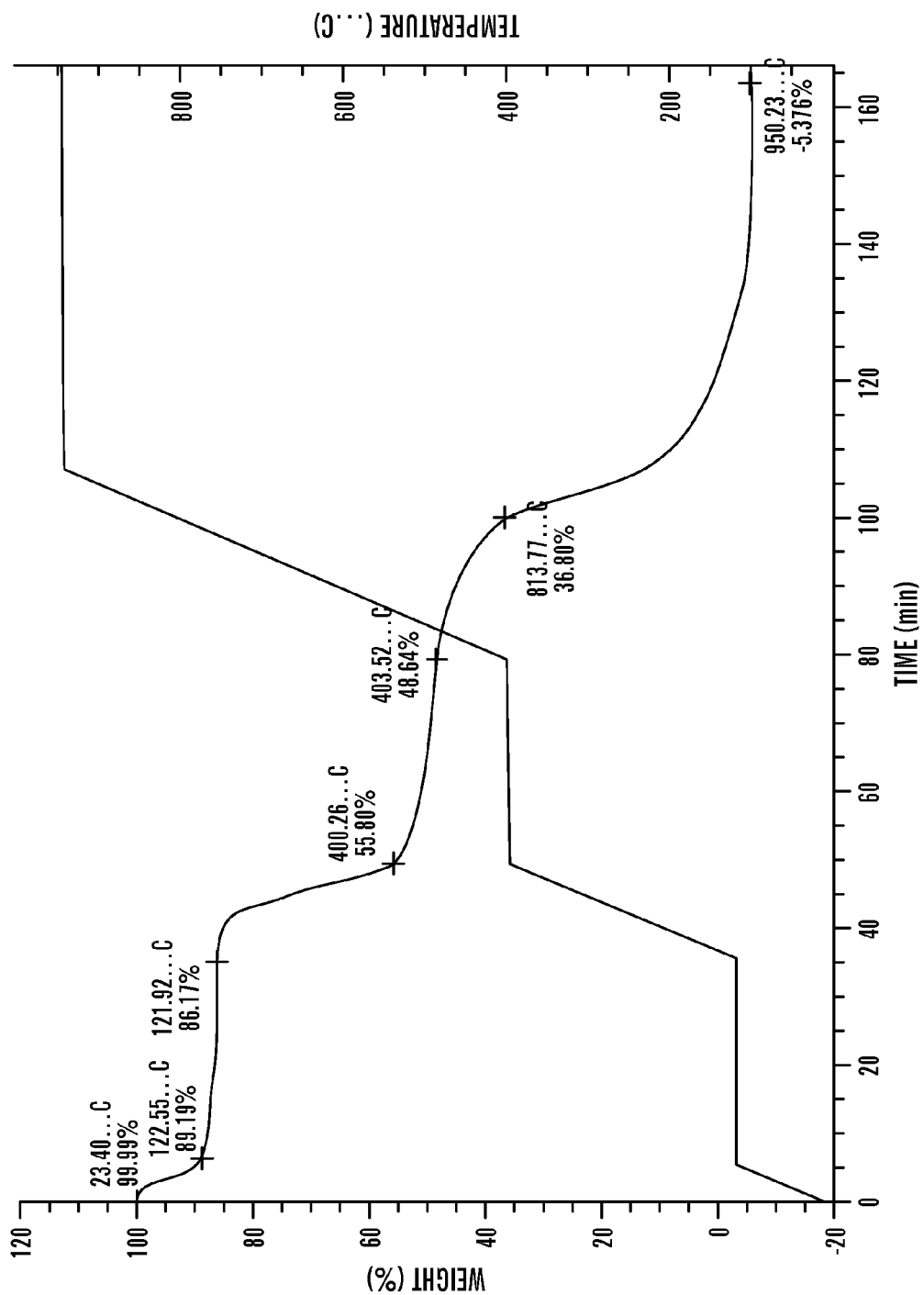
FIG. 23 shows a Thermogravimetric Analysis (TGA) profile of Ag—GdCNTA.

Ag—GdCNTA:

In the percent weight loss curve for Ag—Gd-CNTA, the first sharp loss (19.20%) during the temperature interval of 25° C.-120° C. shows the loss of moisture from the compound. The second percent weight lost step (34.93%) in the temperature interval of 120° C.-810° C. is the loss of organic ligand from the surface of the nanoparticle. The final weight loss step (65.07%) in the temperature interval of 810° C.-950° C. is the inorganic silver nanoparticle. See FIG. 23.

The TGA profiles for all the compounds show the loss of moisture in the first step followed by the decomposition of the organic ligand and, lastly, the inorganic metal. These profiles are comparable to results found by Kim et al. for their amino acid covered gold nanoparticles. See Joo, T. H., et al., *Chemical Physics Letters*, 112 (1): 65-68 (1984), which is hereby incorporated by reference in its entirety.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims that follow.

What is claimed:

1. A multivalent product comprising:

a nanoparticle comprising a metal, metal alloy, or metal oxide core;

a plurality of ligands bound to the nanoparticle, said ligands selected from the group consisting of cysteine N,N'-tetraacetic acid; diethylenetriaminepentaacetic acid-L-Cys; diethylenetriaminepentaacetic acid lipoic acid; 1,4,7,10-tetracarboxymethyl-1,4,7,10-tetraazacyclododecane-L-Cys; 1,4,7,10-tetracarboxymethyl-1,4,7,10-tetraazacyclododecane-lipoic acid; 2,2'-((2-((1-carboxy-3-mercaptopropyl)(carboxymethyl)amino)ethyl)azanediyl)diacetic acid;

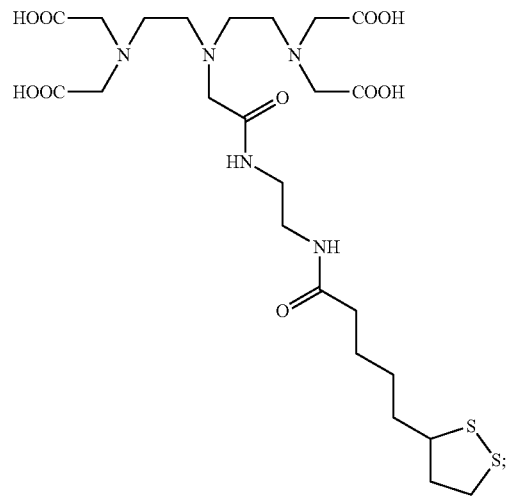 [SMILES: O=C(O)CN(CCN(CCN(CC(=O)O)CC(=O)O)CC(=O)NCCNC(=O)CCCCC1CCSS1)CC(=O)O]

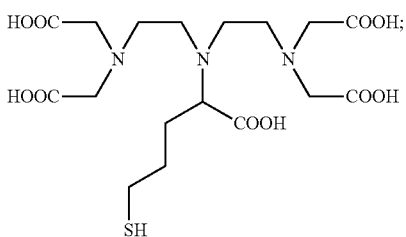 [SMILES: O=C(O)CN(CCN(CCN(CC(=O)O)CC(=O)O)C(CCCS)C(=O)O)CC(=O)O]

and mixtures thereof; and
a plurality of paramagnetic ions coupled to the nanoparticle by the ligands.

2. A multivalent product comprising:
   a nanoparticle comprising a metal, metal alloy, or metal oxide core and
   a monolayer attached to the nanoparticle, said monolayer comprising:
      a plurality of ligands each bound to the nanoparticle and
      a plurality of paramagnetic ions each coupled to the nanoparticle by the ligands, wherein the ligands are selected from the group consisting of cysteine N,N'-tetraacetic acid: diethylenetriaminepentaacetic acid-L-Cys; diethylenetriaminepentaacetic acid lipoic acid; 1,4,7,10-tetracarboxymethyl-1,4,7,10-tetraaza-cyclododecane-L-Cys; 1,4,7,10-tetracarboxymethyl-1,4,7,10-tetraazacyclododecane-lipoic acid; 2,2'-((2-((1-carboxy-3-mercaptopropyl)(carboxymethyl)amino)ethyl)azanediyl)diacetic acid;

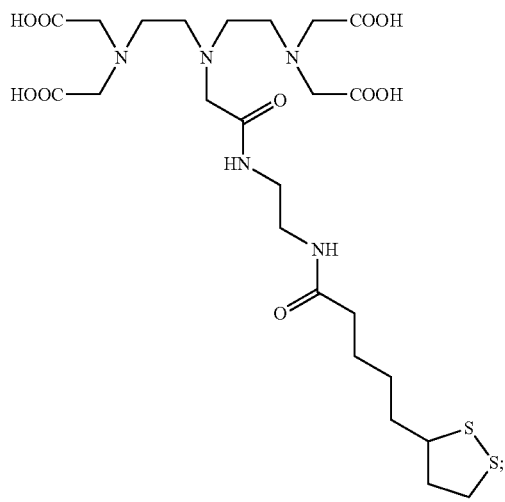 [SMILES: O=C(O)CN(CCN(CCN(CC(=O)O)CC(=O)O)CC(=O)NCCNC(=O)CCCCC1CCSS1)CC(=O)O]

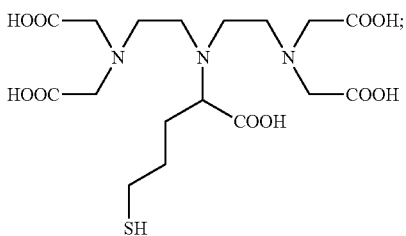 [SMILES: O=C(O)CN(CCN(CCN(CC(=O)O)CC(=O)O)C(CCCS)C(=O)O)CC(=O)O]

and mixtures thereof.

3. The product of claim 2, wherein the nanoparticle has a shape that is spherical, rod shaped, or polyhedral.

4. The product of claim 2, wherein the metal in the nanoparticle is selected from the group consisting of gold, silver, copper, platinum, iron, and mixtures thereof.

5. The product of claim 4, wherein the metal is gold.
6. The product of claim 4, wherein the metal is silver.
7. The product of claim 4, wherein the metal is copper.
8. The product of claim 4, wherein the metal is platinum.
9. The product of claim 4, wherein the metal is iron.
10. The product of claim 9, wherein the iron is present in the nanoparticle as an iron oxide selected from the group consisting of FeO, $Fe_2O_3$, $Fe_3O_4$, and mixtures thereof.
11. The product of claim 2, wherein the paramagnetic ions are selected from group consisting of ions of the lanthanide series, ions of the transition metal series, and mixtures thereof.
12. The product of claim 11, wherein the paramagnetic ions are selected from the group consisting of ions of iron, ions of gadolinium, ions of europium, ions of manganese, ions of dysprosium, ions of ytterbium, ions of lanthanum, ions of lutetium, and mixtures thereof.
13. The product of claim 11, wherein the paramagnetic ion is an ion of gadolinium.
14. The product of claim 11, wherein the paramagnetic ion is an ion of europium.
15. The product of claim 2 further comprising:
   a plurality of polyethylene glycol (PEG) molecules attached to the nanoparticle.
16. The product of claim 2 further comprising:
   a plurality of alkane thiol molecules attached to the nanoparticle.
17. The product of claim 2 further comprising:
   a plurality of peptides containing cysteine attached to the particle.
18. The product of claim 2 further comprising:
   a plurality of radioisotope molecules attached to the nanoparticle.
19. A method of making a multivalent product, said method comprising:
   providing a non-polymerizing ligand;
   providing a paramagnetic ion;
   contacting the ligand and the paramagnetic ion under conditions effective to form a paramagnetic ion-ligand complex;
   providing a solution of nanoparticles comprising a metal, metal alloy, or metal oxide core; and
   contacting the paramagnetic ion-ligand complex and the nanoparticles under conditions effective to form the multivalent product, said multivalent product comprising:
      a nanoparticle comprising a metal, metal alloy, or metal oxide core and
      a monolayer attached to the nanoparticle, said monolayer comprising:
         a plurality of ligands each bound to the nanoparticle and
         a plurality of paramagnetic ions each coupled to the nanoparticle by the ligands, wherein the ligands are selected from the group consisting of cysteine N,N'-tetraacetic acid; diethylenetriaminepentaacetic acid-L-Cys; diethylenetriaminepentaacetic acid lipoic acid; 1,4,7,10-tetracarboxymethyl-1,4,7,10-tetraaza-cyclododecane-L-Cys; 1,4,7,10-tetracarboxymethyl-1,4,7,10-tetraazacyclododecane-lipoic acid; 2,2'-((2-((1-carboxy-3-mercaptopropyl)(carboxymethyl)amino)ethyl)azanediyl)diacetic acid;

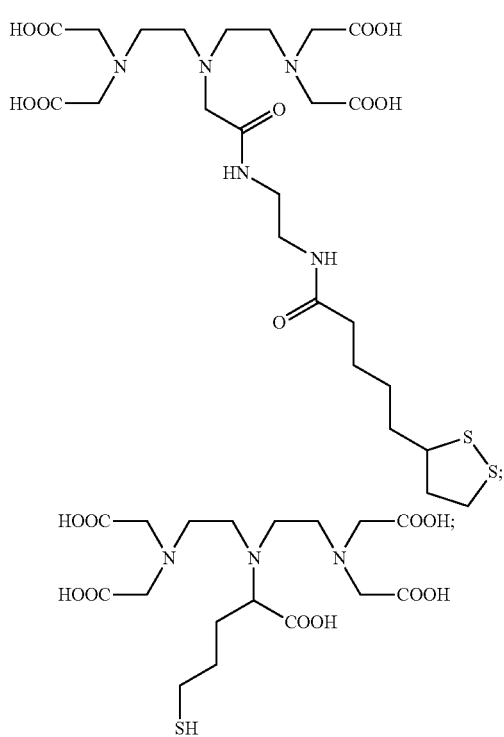

and mixtures thereof.

20. The method of claim 19 further comprising:
providing a radioisotope; and
contacting the radioisotope and the nanoparticles under conditions effective to radio-label the multivalent product.

21. A method of imaging a subject comprising:
providing the multivalent product of claim 2;
providing a subject to be imaged;
contacting the multivalent product and the subject; and
imaging said subject using the multivalent product.

22. The method of imaging of claim 21, wherein said imaging comprises magnetic resonance imaging, fluorescence imaging, surfaced enhance Raman imaging, radiologic imaging, or the targeted delivery of radioisotopes.

23. The method of imaging of claim 22, wherein said targeted delivery of radioisotopes is to tumors.

24. The method of imaging of claim 22, wherein said imaging is carried out in conjunction with a real-time MRI or CT guided procedure.

25. The method of claim 24, wherein the procedure is a surgical procedure.

26. The method of claim 24, wherein the surgical procedure comprises balloon angioplasty or catheterization.

* * * * *